US008158128B2

(12) United States Patent
Grimes

(10) Patent No.: US 8,158,128 B2
(45) Date of Patent: Apr. 17, 2012

(54) MONOCLONAL ANTIBODIES TO PROGASTRIN

(75) Inventor: Stephen Grimes, Davis, CA (US)

(73) Assignee: Cancer Advances, Inc., Durham, NC (US)

(*) Notice: Subject to any disclaimer, the term of this patent is extended or adjusted under 35 U.S.C. 154(b) by 681 days.

(21) Appl. No.: 11/663,126

(22) PCT Filed: Sep. 21, 2005

(86) PCT No.: PCT/IB2005/002793
§ 371 (c)(1),
(2), (4) Date: Mar. 16, 2007

(87) PCT Pub. No.: WO2006/032980
PCT Pub. Date: Mar. 30, 2006

(65) Prior Publication Data
US 2007/0248608 A1    Oct. 25, 2007

Related U.S. Application Data

(60) Provisional application No. 60/612,224, filed on Sep. 22, 2004.

(51) Int. Cl.
*G01N 33/53* (2006.01)
*C07K 14/00* (2006.01)

(52) U.S. Cl. ............... 424/158.1; 424/183.1; 530/350; 530/387.3; 435/7.94

(58) Field of Classification Search ............ None
See application file for complete search history.

(56) References Cited

U.S. PATENT DOCUMENTS

| | | | |
|---|---|---|---|
| 3,931,141 A | 1/1976 | Wissmann | 530/329 |
| 4,069,313 A | 1/1978 | Woodhour et al. | |
| 4,196,265 A | 4/1980 | Koprowski | 435/2 |
| 4,201,770 A | 5/1980 | Stevens | 424/177 |
| 4,302,386 A | 11/1981 | Stevens | 260/112.5 |
| 4,384,995 A | 5/1983 | Stevens | 260/112.5 |
| 4,526,716 A | 7/1985 | Stevens | 260/112.5 |
| 4,565,805 A | 1/1986 | Smirnov | 514/17 |
| 4,687,759 A | 8/1987 | Martinez et al. | |
| 4,691,006 A | 9/1987 | Stevens | 530/324 |
| 4,762,913 A | 8/1988 | Stevens | 530/345 |
| 4,767,842 A | 8/1988 | Stevens | 530/324 |
| 4,794,103 A | 12/1988 | Bertolini | 514/12 |
| 4,803,170 A | 2/1989 | Stanton et al. | 436/518 |
| 4,816,567 A | 3/1989 | Cabilly et al. | 530/387 |
| 4,840,939 A | 6/1989 | Leveen et al. | |
| 4,894,443 A | 1/1990 | Greenfield et al. | |
| 4,923,819 A | 5/1990 | Fernandez et al. | |
| 4,925,922 A | 5/1990 | Byers et al. | |
| 4,971,792 A | 11/1990 | Steplewski et al. | 424/1.49 |
| 4,978,683 A | 12/1990 | Rovati et al. | 514/617 |
| 4,997,950 A | 3/1991 | Murphy et al. | 548/304.1 |
| 5,006,334 A | 4/1991 | Stevens | 424/88 |
| 5,023,077 A | 6/1991 | Gevas et al. | 424/88 |
| 5,035,988 A | 7/1991 | Nakamura et al. | |
| 5,055,404 A | 10/1991 | Ueda et al. | |
| 5,110,911 A | 5/1992 | Samuel et al. | 530/395 |
| 5,120,829 A | 6/1992 | Pierschbacher et al. | |
| 5,162,504 A | 11/1992 | Horoszewisz | |
| 5,164,299 A | 11/1992 | Lambert | |
| 5,242,799 A | 9/1993 | Samuel et al. | 435/7.1 |
| 5,256,542 A | 10/1993 | Chang | |
| 5,319,073 A | 6/1994 | Wank | |
| 5,468,494 A | 11/1995 | Gevas et al. | 424/195.11 |
| 5,484,596 A | 1/1996 | Hanna, Jr. et al. | |
| 5,580,563 A | 12/1996 | Tam et al. | |
| 5,585,474 A | 12/1996 | Iwaki et al. | |
| 5,607,676 A | 3/1997 | Gevas et al. | 424/197.11 |
| 5,609,870 A | 3/1997 | Gevas et al. | 424/184.1 |
| 5,622,702 A | 4/1997 | Gevas et al. | 424/184.1 |
| 5,639,613 A | 6/1997 | Shay et al. | |

(Continued)

FOREIGN PATENT DOCUMENTS

EP    380230    11/1994

(Continued)

OTHER PUBLICATIONS

Pauwel et al. J.Clin. Invest., 1986, vol. 77, p. 376-381.*
Kipriyanov et al., Mol. Biol. 1999, vol. 12, p. 173-197.*
Dockray et al., "The Gastrins: Their Production and Biological Activities," Annu. Rev. Physiol. vol. 63 pp. 119-139 (2001).
Hughes et al., "Therapy with Gastrin Antibody in the Zollinger-Ellison Syndrome," Digestive Diseases. vol. 21, No. 3 pp. 201-204 (1976).
Joshi, S.N., and Gardner, J.D., "Gastrin and Colon Cancer: A Unifying Hypothesis," Digistive Diseases. vol. 14 pp. 334-344 (1996).
Smith, A.M., and Watson, S. A., "Review article: gastrin and colorectal cancer," Aliment Pharmacol. Ther. vol. 14 pp. 1231-1247 (2000).

(Continued)

*Primary Examiner* — Yunsoo Kim
(74) *Attorney, Agent, or Firm* — Jenkins, Wilson, Taylor & Runt, P.A.

(57) ABSTRACT

The present invention provides progastrin-binding molecules specific for progastrin that do not bind gastrin-17(G17), gastrin-34(G34), glycine-extended gastrin-17(G17-Gly), or glycine-extended gastrin-34(G34-Gly). Further, the invention provides monoclonal antibodies (MAbs) selective for sequences at the N-terminus and the C-terminus of the gastrin precursor molecule, progastrin and the hybridomas that produce these MAbs. Also provided are panels of Mabs useful for the detection and quantitation of progastrin and gastrin hormone species in immuno-detection and quantitation assays. These assays are useful for diagnosing and monitoring a gastrin-promoted disease or condition, or for monitoring the progress of a course of therapy. The invention further provides solid phase assays including immunohistochemical (IHC) and immunofluorescence (IF) assays suitable for detection and visualization of gastrin species in solid samples, such as biopsy samples or tissue slices. The progastrin-binding molecules are useful therapeutically for passive immunization against progastrin in progastrin-promoted diseases or conditions. Also provided are surrogate reference standard (SRS) molecules that are peptide chains of from about 10 to about 35 amino acids, wherein the SRS molecule comprises at least two epitopes found in a protein of interest of greater than about 50 amino acids. Such SRS molecules are useful as standards in place of authentic proteins of interest.

25 Claims, No Drawings

U.S. PATENT DOCUMENTS

| | | | |
|---|---|---|---|
| 5,643,735 A | 7/1997 | Yokoi et al. | 435/7.9 |
| 5,665,864 A | 9/1997 | Quaranta et al. | 530/387.1 |
| 5,665,874 A | 9/1997 | Kuhajda et al. | |
| 5,668,117 A | 9/1997 | Shapiro | |
| 5,683,695 A | 11/1997 | Shen et al. | 424/185.1 |
| 5,688,506 A | 11/1997 | Grimes et al. | 424/184.1 |
| 5,698,201 A | 12/1997 | Stevens | 424/195.11 |
| 5,703,213 A | 12/1997 | Wands et al. | 530/388.85 |
| 5,712,369 A | 1/1998 | Old et al. | |
| 5,723,718 A | 3/1998 | Berens | |
| 5,731,159 A | 3/1998 | Waldman | 435/7.23 |
| 5,733,790 A | 3/1998 | Potter et al. | |
| 5,736,146 A | 4/1998 | Cohen et al. | 424/194.11 |
| 5,750,119 A | 5/1998 | Srivastava | 424/277.1 |
| 5,759,551 A | 6/1998 | Ladd et al. | 424/198.1 |
| 5,759,791 A | 6/1998 | Kuhajda et al. | |
| 5,767,242 A | 6/1998 | Zimmerman et al. | |
| 5,770,576 A | 6/1998 | Morozov et al. | |
| 5,785,970 A | 7/1998 | Gevas et al. | 424/184.1 |
| 5,786,213 A | 7/1998 | Singh et al. | 435/320.1 |
| 5,788,964 A | 8/1998 | Baral et al. | |
| 5,827,691 A | 10/1998 | Iwaki et al. | |
| 5,843,446 A | 12/1998 | Ladd et al. | 424/184.1 |
| 5,866,128 A | 2/1999 | Gevas et al. | 424/184.1 |
| 5,869,045 A | 2/1999 | Hellstrom et al. | 424/130.1 |
| 5,869,058 A | 2/1999 | Cohen et al. | 424/194.11 |
| 5,879,898 A | 3/1999 | Tarin et al. | 435/7.21 |
| 5,932,412 A | 8/1999 | Dillner et al. | 435/5 |
| 5,981,167 A | 11/1999 | Taremi et al. | 435/4 |
| 6,132,720 A | 10/2000 | Grimes et al. | |
| 6,169,173 B1 | 1/2001 | Wank | 536/23.5 |
| 6,180,370 B1 | 1/2001 | Queen et al. | |
| 6,187,536 B1 | 2/2001 | Weinberg et al. | 435/6 |
| 6,191,290 B1 | 2/2001 | Safavy | |
| 6,251,581 B1 | 6/2001 | Ullman et al. | 435/4 |
| 6,303,123 B1 | 10/2001 | Grimes et al. | |
| 6,320,022 B1 | 11/2001 | Cutitta et al. | |
| 6,359,114 B1 | 3/2002 | Grimes et al. | 530/344 |
| 6,391,299 B1 | 5/2002 | Blackburn et al. | 424/133.1 |
| 6,548,066 B1 | 4/2003 | Michaeli et al. | 424/185.1 |
| 6,565,813 B1 | 5/2003 | Garyantes | 422/102 |
| 6,613,530 B1 | 9/2003 | Wienhues et al. | 435/7.1 |
| 6,627,196 B1 | 9/2003 | Baughman et al. | |
| 6,639,055 B1 | 10/2003 | Carter et al. | 530/387.1 |
| 6,689,869 B2 | 2/2004 | Waldmann et al. | 530/388.75 |
| 6,696,262 B2 | 2/2004 | Harkonen | 435/7.32 |
| 6,699,974 B2 | 3/2004 | Ono et al. | 530/388.85 |
| 6,780,969 B2 | 8/2004 | Wang | 530/324 |
| 6,815,414 B2 | 11/2004 | Chowers et al. | 514/8 |
| 6,861,510 B1 | 3/2005 | Gevas et al. | 530/388.1 |
| 7,074,761 B1 | 7/2006 | Hinuma et al. | |
| RE39,586 E | 4/2007 | Dagan | |
| 7,235,376 B2 | 6/2007 | Grimes et al. | |
| 7,300,918 B2* | 11/2007 | Rath | 514/2 |
| 7,438,907 B2 | 10/2008 | Schuurman et al. | |
| 7,662,926 B2 | 2/2010 | Chan et al. | |
| 7,964,371 B2 | 6/2011 | Grimes et al. | |
| 2001/0020005 A1 | 9/2001 | Chowers et al. | 514/8 |
| 2002/0058040 A1 | 5/2002 | Grimes et al. | 424/185.1 |
| 2002/0095028 A1 | 7/2002 | Grimes et al. | 530/412 |
| 2003/0021786 A1 | 1/2003 | Gevas et al. | 424/146.1 |
| 2003/0049698 A1 | 3/2003 | Wang | 435/7.21 |
| 2003/0068326 A1 | 4/2003 | Gevas et al. | 424/185.1 |
| 2003/0082643 A1 | 5/2003 | Hudson et al. | 435/7.21 |
| 2003/0086941 A1 | 5/2003 | Michaeli et al. | 424/185.1 |
| 2003/0091574 A1 | 5/2003 | Gevas et al. | 424/155.1 |
| 2003/0138860 A1 | 7/2003 | Robertson et al. | 435/7.23 |
| 2003/0232399 A1 | 12/2003 | Robertson et al. | 435/7.23 |
| 2004/0001842 A1 | 1/2004 | Michaeli et al. | 424/185.1 |
| 2004/0063164 A1 | 4/2004 | Lassalle | |
| 2004/0266682 A1 | 12/2004 | Cruz | |
| 2005/0025770 A1 | 2/2005 | Gevas et al. | 424/155.1 |
| 2005/0069966 A1 | 3/2005 | Grimes et al. | 435/7.92 |
| 2005/0169979 A1 | 8/2005 | Michaeli et al. | 424/184.1 |
| 2005/0187152 A1 | 8/2005 | Gevas et al. | 514/12 |
| 2006/0020119 A1 | 1/2006 | Grimes et al. | 530/388.24 |
| 2006/0039911 A1 | 2/2006 | Gevas et al. | 424/145.1 |
| 2006/0140962 A1 | 6/2006 | Gevas et al. | 424/155.1 |
| 2007/0031511 A1 | 2/2007 | Baldwin et al. | 424/653 |
| 2007/0065454 A1 | 3/2007 | Michaeli et al. | 424/184.1 |
| 2007/0082043 A1 | 4/2007 | Michaeli et al. | 424/184.1 |
| 2009/0191232 A1 | 7/2009 | Gevas et al. | |
| 2010/0129382 A1 | 5/2010 | Gevas et al. | |
| 2011/0117108 A1 | 5/2011 | Gevas et al. | |

FOREIGN PATENT DOCUMENTS

| | | |
|---|---|---|
| EP | 0 755 683 | 1/1997 |
| EP | 0 818 680 | 1/1998 |
| EP | 1 129 724 | 9/2001 |
| EP | 1 579 863 | 9/2005 |
| JP | 06107564 A | 4/1994 |
| WO | WO90/08774 | 8/1990 |
| WO | WO94/00590 | 1/1994 |
| WO | WO95/04544 | 2/1995 |
| WO | WO 95/13297 | 5/1995 |
| WO | WO95/21380 | 8/1995 |
| WO | WO96/15456 | 5/1996 |
| WO | WO97/28821 | 8/1997 |
| WO | WO97/38584 | 10/1997 |
| WO | WO98/31393 | 7/1998 |
| WO | WO98/51337 | 11/1998 |
| WO | WO99/19353 | 4/1999 |
| WO | WO 99/59628 | 11/1999 |
| WO | WO99/59631 | 11/1999 |
| WO | WO99/65513 | 12/1999 |
| WO | WO00/67035 | 11/2000 |
| WO | WO 01/13114 | 2/2001 |
| WO | WO 01/34192 | 5/2001 |
| WO | WO 01/77685 | 10/2001 |
| WO | WO02/39123 | 5/2002 |
| WO | WO 2004/023148 | 3/2004 |
| WO | WO2004/088326 | 10/2004 |
| WO | WO 2005/095459 | 10/2005 |
| WO | WO 2006/008649 | 1/2006 |
| WO | WO 2006/016275 | 2/2006 |
| WO | WO2007/062531 | 6/2007 |

OTHER PUBLICATIONS

Ajani et al., "An Open-Label, Multinational, Multicenter Study of G17DT Vaccination Combined with Cisplatin and 5-Fluorouracil in Patients with Untreated, Advanced Gastric or Gastroesophageal Cancer: The GC4 Study," Cancer. vol. 106, No. 9 pp. 1908-1916 (2006).

Bailey, "Radioimmunoassay of Peptides and Proteins," Methods in Molecular Biology. vol. 32 pp. 449-459 (1994).

Cole, "Immunoassay of human chorionic gonadotropin, its free subunits, and metabolites," Clinical Chemistry. vol. 43, No. 12 pp. 2233-2243 (1997).

Demeester et al., "Patterns of Gastroesophageal Reflux in Health and Disease," Ann. Surg. vol. 184, No. 4 pp. 459-469 (1976).

Dickinson, C.J., and Yamada, T., "Gastrin-amidating Enzyme in the Porcine Pituitary and Antrum," The Journal of Biological Chemistry. vol. 266, No. 1 pp. 334-338 (1991).

Du et al. "Biochip as a potential platform of serological interferon α2b antibody assay," Journal of Biotechnology. vol. 106, No. 1 pp. 87-100 (2003).

He, A.R., and Marshall, J.L., "Clinical experiences with G17DT in gastrointestinal malignancies," Expert Rev. Anticancer Ther. vol. 6, No. 4 pp. 487-492 (2006) [Abstract].

Hsi, "A Practical Approach for Evaluating New Antibodies in the Clinical Immunohistochemistry Laboratory," Arch. Pathol. Lab. Med. vol. 125 pp. 289-294 (2001).

International Preliminary Examination Report corresponding to International Patent Application No. PCT/US2002/008756 dated May 26, 2006.

International Preliminary Report on Patentability corresponding to International Patent Application No. PCT/US2004/09666 dated Jan. 19, 2006.

International Preliminary Report on Patentability corresponding to International Patent Application No. PCT/US2005/002793 dated Aug. 7, 2007.

International Search Report corresponding to International Patent Application No. PCT/US1990/000520 dated May 21, 1990.

International Search Report corresponding to International Patent Application No. PCT/US1999/010751 dated Oct. 19, 1999.

International Search Report corresponding to International Patent Application No. PCT/US2005/010532 dated Feb. 8, 2006.
Janeway et al. "Immunobiology: The Immune System in Health and Disease," Fourth Edition, Elsevier Science Ltd./Garland Publishing, New York, NY p. 544 (1999).
Jonsson, A., and Dockray, G.J., "Immunohistochemical localization to pyloric antral G cells of peptides derived from porcine preprogastrin," Regulatory Peptides. vol. 8 pp. 283-290 (1984).
Landis et al., "Cancer Statistics, 1998" Ca. Cancer J. Clin. vol. 48, No. 1 pp. 6-30 (1998).
Official Action corresponding to Australian Patent Application No. 2005286164 dated Feb. 14, 2011.
Official Action corresponding to U.S. Appl. No. 11/499,261 dated Apr. 26, 2011.
Onorato et al., "Immunohistochemical and ELISA Assays for Biomarkers of Oxidative Stress in Aging and Disease," Annals of New York Academy of Sciences. vol. 854 pp. 277-290 (1998).
Osin, P.P., and Lakhani, S.R., "The pathology of familial breast cancer: Immunohistochemistry and molecular analysis," Breast Cancer Research. vol. 1, No. 1 pp. 36-40 (1999).
Plested et al. "ELISA," Methods in Molecular Medicine. vol. 71 pp. 243-261 (2003).
Rondeel, "Immunofluorescence *versus* ELISA for the detection of antinuclear antigens," Expert Rev. Mol. Diagn. vol. 2, No. 3 pp. 226-232 (2002).
Tetin, S.Y., and Stroupe, S.D., "Antibodies in Diagnostic Applications," Current Pharmaceutical Biotechnology. vol. 5, No. 1 pp. 9-16 (2004).
Väänänen et al. "Non-endoscopic diagnosis of atrophic gastritis with a blood test. Correlation between gastric histology and serum levels of gastrin-17 and pepsinogen I: a multicentre study," European Journal of Gastroenterology & Hepatology. vol. 15, No. 8 pp. 885-891 (2003).
Written Opinion corresponding to International Patent Application No. PCT/US2004/009666 dated Nov. 7, 2004.
Abdalla et al., "Gastrin-Induced Cyclooxygenase-2 Expression in Barrett's Carcinogenesis," Clinical Cancer Research. vol. 10 pp. 4784-4792 (2004).
Abrahm et al., "Development and Evaluation of a High Affinity Species and Region Specific Monoclonal Antibody to Human Gastrin," Gastroenterology. vol. 86, No. 5, Part 2 p. 1012 (1984).
Ajani et al., "Phase I and II Studies of the Combination of Recombinant Human Interferon-γ and 5-Fluorouracil in Patients with Advanced Colorectal Carcinoma," Journal of Biological Response Modifiers. vol. 8, No. 2 pp. 140-146 (1989).
Asao et al., "Eradication of Hepatic Metastases of Carcinome H-59 by Combination Chemimmunotherapy with Liposomal Muramyl Tripeptide, 5-Fluorouracil, and Leucovorin," Cancer Research. vol. 52 pp. 6254-6257 (1992).
Ausubel, ed., "Current Protocols in Molecular Biology," John Wiley & Sons, New York, pp. 11.15.1-11.15.9. (2002).
Azuma et al., "Immunocytochemical Evidence for Differential Distribution of Gastrin Forms Using Region-Specific Antibodies," Gastroenterologia Japonica. vol. 21, No. 4 pp. 319-324 (1986).
Baldwin, G.S., and Zhang, Q., "Measurement of Gastrin and Transforming Growth Factor α Messenger RNA Levels in Colonic Carcinoma Cell Lines by Quantitative Polymerase Chain Reaction," Cancer Research. vol. 52 pp. 2261-2267(1992).
Baldwin, G.S. and A. Shulkes, "Gastrin, gastrin receptors and colorectal carcinoma," Gut. vol. 42 pp. 581-584 (1998).
Ballantyne, G.H., and Quin, J., "Surgical Treatment of Liver Metastasis in Patients with Colorectal Cancer," Cancer. vol. 71, No. 12 pp. 4252-4266 (1993).
Beacham et al., "Human Gastrin: Isolation, Structure and Synthesis: Synthesis of Human Gastrin I," Nature. vol. 209, No. 5023 pp. 585-586 (1966).
Beauchamp et al., "Proglumide, A Gastrin Receptor Antagonist, Inhibits Growth of Colon Cancer and Enhances Survival in Mice," Ann. Surg. vol. 202, No. 3 pp. 303-308 (1985).
Behr et al., "Cholecystokinin-B/Gastrin Receptor Binding Peptides: Preclinical Development and Evaluation of Their Diagnostic and Therapeutic Potential," Clinical Cancer Research. vol. 5 pp. 3124s-3138s (1999).

Beinborn et al., "A single amino acid of the cholecystokinin-B/gastrin receptor determines specificity for non-peptide antagonists," Nature. vol. 362 pp. 348-350 (1993).
Biagini et al., "The Human Gastrin/Cholecystokinin Receptors: Type B and Type C Expression in Colonic Tumours and Cell Lines," Life Sciences. vol. 61, No. 10 pp. 1009-1018 (1997).
Blackmore et al. "Autocrine Growth Stimulation of Human Renal Wilms' Tumour G401 Cells by a Gastrin-Like Peptide," International Journal of Cancer. vol. 57 pp. 385-393 (1994).
Bodey, "The significance of immunohistochemistry in the diagnosis and therapy of neoplasms," Expert Opin. Biol. Ther. vol. 2, No. 4 pp. 371-393 (2002).
Boland, "Editiorial: Gastrin and Colorectal Neoplasia—Chicken or Egg, or Both?" J. Clin. Gastroenterology. vol. 13, No. 5 pp. 497-499 (1991).
Boon, "Toward a Genetic Analysis of Tumor Rejection Antigens," Advances in Cancer Research. vol. 58 pp. 177-210 (1992).
Bowie et al., "Deciphering the Message in Protein Sequences: Tolerance to Amino Acid Substitutions," Science. vol. 247 pp. 1306-1310 (1990).
Buchan et al., "Regulatory Peptides in Barrett's Esophagus," Journal of Pathology. vol. 146, No. 3 pp. 227-234 (1985).
Burris III et al., "Improvements in survival and clinical benefit with gemcitabine as first-line therapy for patients with advanced pancreas cancer: a randomized trial," Journal of Clinical Oncology. vol. 15, No. 6 pp. 2403-2413 (1997).
Bystryn, J., "Tumor vaccines," Cancer and Metastasis Reviews. vol. 9 pp. 81-91 (1990).
Caplin et al., "Expression and processing of gastrin in pancreatic adenocarcinoma," Brit. J. Surgery. vol. 87 pp. 1035-1040 (2000).
Casper et al., "Phase II trial of gemcitabine (2,2'-difluorodeoxycitidine) in patients with adenocarcinoma of the pancreas," Investigational New Drugs. vol. 12, No. 1 pp. 29-34 (1994) [Abstract].
Chaudhry et al., "Phase I and Imaging Trial of a Monoclonal Antibody Directed Against Gastrin-releasing Peptide in Patients with Lung Cancer," Clinical Cancer Researc. vol. 5 pp. 3385-3393 (1999).
Choudhury et al., "*N*-Terminal Sequence of Human Big Gastrin: Sequence, Synthetic and Immunochemical Studies," A76 Hoppe-Seyler's Z. Physiol. Chem. vol. 361 pp. 1719-1733 (1980).
Ciccotosto et al., "Expression, Processing, and Secretion of Gastrin in Patients With Colorectal Carcinoma," Gastroenterology. vol. 109, No. 4 pp. 1142-1153 (1995).
Clerc et al., "Differential Expression of the CCK-A and CCK-B/Gastrin Receptor Genes in Human Cancers of the Esophagus, Stomach, and Colon," International Journal of Cancer. vol. 72 pp. 931-936 (1997).
de Jong et al., "Effects of partial liver resection on tumor growth," Journal of Hepatology. vol. 25 pp. 109-121 (1996).
De Magistris, L., and Rehfeld, J.F., "A Simple Enzymatic Procedure for Radioimmunochemical Quantitation of the Large Molecular Forms of Gastrin and Cholecystokinin," Analytical Biochemistry. vol. 102 pp. 126-133 (1980).
Dethloff et al., "Inhibition of Gastrin-Stimulated Cell Proliferation by the CCK-B/gastrin Receptor Ligand CI-988," Food and Chemical Toxicology. vol. 37 pp. 105-110 (1999).
Dickinson, C.J., "Relationship of Gastrin Processing to Colon Cancer," Gastroenterology. vol. 109, No. 4 pp. 1384-1388 (1995).
Dockray, G.J., and Walsh, J.H., "Amino-Terminal Gastrin Fragment in Serum of Zollinger-Ellison Syndrome Patients," Gastroenterology. vol. 68, No. 2 pp. 222-230 (1975).
Dockray et al., "Gastric Endocrine Cells: Gene Expression, Processing, and Targeting of Active Products," Physiological Review. vol. 76, No. 3 pp. 767-798 (1996).
Dockray et al., "Immunochemical studies on big gastrin using $NH_2$-terminal specific antiserums," Regulatory Peptides. vol. 1, No. 3 pp. 169-186 (1980). Chemical Abstracts vol. 94 pp. 506-507 (1981) [Abstract •94:119200w].
Dockray et al., "The Gastrins: Their Production and Biological Activities," Ann. Rv. Physiol. vol. 63 pp. 119-139 (2001).
Dockray, G.J., and Taylor, I.L., "Heptadecapeptide Gastrin: Measurement in Blood by Specific Radioimmunoassay", Gastroenterology. vol. 71, No. 6 pp. 971-977 (1976).

Dockray, "Immunochemical Studies on Big Gastrin Using $NH_2$-Terminal Specific Antisera," Regulatory Peptides. vol. 1 pp. 169-186 (1980).

Douziech et al. "Growth Effects of Regulatory Peptides and Intracellular Signaling Routes in Human Pancreatic Cancer Cell Lines," Endocrine. vol. 9, No. 2 pp. 171-183 (1998).

Edkins, J.S., "On the Chemical Mechanism of Gastric Secretion," Proceedings of the Royal Society of London. Series B, Containing Papers of a Biological Character. vol. 76, No. 510 p. 376 (1905).

Edkins, J.S., "The Chemical Mechanism of Gastric Secretion," J. Physiol. vol. 34, Nos. 1-2 pp. 133-144 (1906).

Erlichman et al., "A Randomized Trial of Fluorouracil and Colonic Acid in Patients With Metastatic Colorectal Carcinoma," Journal of Clinical Oncology. vol. 6 pp. 469-475 (1988).

Ezzell, C., "Cancer 'Vaccines': An Idea Whose Time Has Come?" The Journal of NIH Research. vol. 7 pp. 46-49 (1995).

Feurle et al. "The Role of CCK and its Analogues in the Organogenesis of the Fetal Rat Pancreas," Pancreas. vol. 10, No. 3 pp. 281-286 (1995).

Finley et al., "Expression of the Gastrin Gene in the Normal Human Colon and Colorectal Adenocarcinoma," Cancer Research. vol. 53 pp. 2919-2926 (1993).

Fourmy et al., "Relationship of CCK/gastrin-receptor binding to amylase release in dog pancreatic acini," Regulatory Peptides. vol. 10 pp. 57-68 (1984).

Frucht et al., "Characterization of Functional Receptors for Gastrointestinal Hormones on Human Colon Cancer Cells," Cancer Research. vol. 52, No. 5 pp. 1114-1122 (1992).

Gocyk et al. "*Helicobacter pylori*, gastrin and cyclooxygenase-2 in lung cancer," Med. Sci. Monit. vol. 6, No. 6 pp. 1085-1092 (2000).

Goletti et al. "Resection of Liver Gastrinoma Leading to Persistent Eugastrinemia," Eur. J. Surgery. vol. 158 pp. 55-57 (1992).

Gregory, R.A., and Tracy, H.J., "Isolation of Two Gastrins from Human Antral Mucosa," Nature. vol. 209, No. 5023 p. 583 (1966).

Grider, J.R., and Makhlouf, G.M., "Distinct receptors for cholecystokinin and gastrin on muscle cells of stomach and gallbladder," Am. J. Physiol. vol. 259 pp. G184-G190 (1990).

Gupta, J.R., and Siber, G.R., "Adjuvants for human vaccines—current status, problems and future prospects," Vaccine. vol. 13, No. 14 pp. 1263-1276 (1995).

Gura, T., "Systems for Identifying New Drugs Are Often Faulty," Science. vol. 278, No. 5340 pp. 1041-1042 (1997).

Haigh et al. "Gastrin Induces Proliferation in Barrett's Metaplasia Through Activation of the $CCK_2$ Receptor," Gastroenterology. vol. 124 pp. 615-625 (2003).

Halter et al., "Evaluation of a Monoclonal Anti-Gastrin Antibody as a Tool for Immunoneutralization of Gastrin During Omeprazole Treatment in the Rat," Gastroenterology. vol. 96, No. 5, Part 2 p. A194 (1989).

Helander et al., "Immunohistochemical localization of gastrin/CCK-B receptors in the dog and guinea-pig stomach," Acta Physiologica Scandinavica. vol. 159, No. 4 pp. 313-320 (1997).

Hellmich et al., "Human Colorectal Cancers Express a Constitutively Active Cholecystokinin-B/Gastrin Receptor That Stimulates Cell Growth," The Journal of Biological Chemistry. vol. 275, No. 41 pp. 32122-32128 (2000).

Henwood et al., "Expression of gastrin in developing gastric adenocarcinoma," British Journal of Surgery. vol. 88 pp. 564-568 (2001).

Herbert et al. (Eds.) "The Dictionary of Immunology," $3^{rd}$ Ed. Academic Press, London, p. 41 (1995).

Herget et al., "Cholecystokinin Stimulates $Ca^{2+}$ Mobilization and Clonal Growth in Small Cell Lung Cancer through $CCK_A$ and $CCK_B$/Gastrin Receptors," Annals New York Academy of Sciences. vol. 713, pp. 283-297 (1994).

Hoosein et al., "Antiproliferative Effects of Gastrin Receptor Antagonists and Antibodies to Gastrin on Human Colon Carcinoma Cell Lines," Cancer Research. vol. 48 pp. 7179-7183 (1988).

Hoosein et al., "Evidence for Autocrine Growth Stimulation of Cultured Colon Tumor Cells by a Gastrin/Cholecystokinin-like Peptide," Experimental Cell Research. vol. 186, No. 1 pp. 15-21 (1990).

Houghten et al., "Relative Importance of Position and Individual Amino Acid Residues in Peptide Antigen-Antibody Interactions: Implications in the Mechanism of Antigenic Drift and Antigenic Shift," Vaccines. vol. 86 pp. 21-25 (1986).

Hughes et al., "Therapy with Gastrin Antibody in the Zollinger-Ellison Syndrome," Digestive Diseases. vol. 21 pp. 201-204 (1976).

Hughes et al., "Development of a class of selective cholecystokinin type B receptor antagonists having potent anxiolytic activity," PNAS. vol. 87 pp. 6728-6732 (1990).

Ichikawa et al., "Distinct effects of tetragastrin, histamine, and CCh on rat gastric mucin synthesis and contribution of NO," Am. J. Physiol. vol. 274, No. 1 pp. G138-G146 (1998).

Iwanaga et al., "Immunocytochemical Localization of the Different Gastrin Forms in the Pyloric Antrum," Biomedical Research. vol. 1 pp. 316-320 (1980).

Iwase et al., "Regulation of Growth of Human Gastric Cancer by Gastrin and Glycine-Extended Progastrin," Gastroenterology. vol. 113 pp. 782-790 (1997).

Jaffe et al., "Gastrin resistance following immunization to the C-terminal tetrapeptide amide of gastrin," Surgery. vol. 69, No. 2 pp. 232-237 (1971).

Jaffe et al., "Inhibition of gastrin activity by incubation with antibodies to the C-terminal tetrapeptide of gastrin," Surgery. vol. 65, No. 4 pp. 633-639 (1969).

Jain, R.K., "Barriers to Drug Delivery in Solid Tumors," Scientific American. vol. 171, No. 1 pp. 58-65 (1994).

Johnson et al, "Ornithine Decarboxylase in Large Bowel Mucosa: Regulation by Gastrin, Secretin and EGF," Journal of Physiology and Pharmacology. vol. 43, No. 1 pp. 33-41 (1992).

Johnson, "New Aspects of the Trophic Action of Gastrointestinal Hormones," Gastroenterology. vol. 72, No. 4, Part 2 pp. 788-792 (1977).

Joshi, S.N., and Gardner, J.D., "Gastrin and Colon Cancer: A Unifying Hypothesis," Digestive Diseases. vol. 14 pp. 334-344 (1996).

Kameyama et al., "Adjuvant Chemo-Endocrine Chemotherapy with Gastrin Antagonist After Resection of Liver Metastasis in Colorectal Cancer," Japanese Journal of Cancer and Chemotherapy. vol. 21, No. 13 pp. 2169-2171 (1994) [Abstract].

Katoh et al., "Malignant Zollinger-Ellison Syndrome. Stabilizing of Liver Metastasis After Gastrectomy with Resection of Primary Tumor," The American Surgeon. vol. 56, No. 6 pp. 360-363 (1990).

Kaufmann et al., "Cholecystokinin B-type receptor signaling is involved in human pancreatic cancer cell growth," Neuropeptides. vol. 31, No. 6 pp. 573-583 (1997).

Kelley et al., "Antitumor Activity of a Monoclonal Antibody Directed Against Gastrin-Releasing Peptide in Patients with Small Cell Lung Cancer," Chest. vol. 112 pp. 256-261 (1997).

Kelly et al., "Pathophysiology of GI Tract and Liver: Expression of progastrin-derived peptides and gastrin receptors in a panel of gastrointestinal carcinoma cell lines," Journal of Gastroenterology and Hepatology. vol. 13 pp. 208-214 (1998).

Kobori et al., "Growth Responses of Rat Stomach Cancer Cells to Gastro-Entero-Pancreatic Hormones," International Journal of Cancer. vol. 30, No. 1 pp. 65-67 (1982).

Kochman et al, "Post-Translational Processing of Gastrin in Neoplastic Human Colonic Tissues," Biochemical and Biophysical Research Communications. vol. 189, No. 2 pp. 1165-1169 (1992).

"Disorder," Stedman's Medical Dictionary $27^{th}$ Edition. http://www.thomsonhc.com/pdrel/librarian/PFDefaultActionId/pdrcommon. Stedmans (1 page), 2009.

Bardram, "Progastrin in Serum from Zollinger-Ellison Patients: An Indicator of Malignancy?" Gastroenterology. vol. 98, No. 6 pp. 1420-1426 (1990).

Gisbert et al., "Decrease in gastrin levels after *H. pylori* eradication," Revista espanola de enfermedades digestives (Spanish Journal of Gastroenterology). vol. 87, No. 2 pp. 99-107 (1995) [Abstract].

Mishell, B.B., and Shiigi, S.M., "Selected Methods in Cellular Immunology," Chapter 17: Immunoglobulin-Producing Hybrid Cell Lines, W.H. Freeman and Co.:San Francisco pp. 368-370 (1980).

Official Action corresponding to Indonesian Patent Application No. WO 00 2007 00931 dated Oct. 5, 2011.

Official Action corresponding to Israeli Patent Application No. 182012 dated Jul. 12, 2011.

Official Action corresponding to Japanese Patent Application No. 2007-506474 dated Jun. 7, 2011.

Official Action corresponding to Japanese Patent Application No. Hei10-549578 dated May 9, 2006.
Official Action corresponding to U.S. Appl. No. 09/700,329 dated Dec. 17, 2001.
Official Action corresponding to U.S. Appl. No. 09/700,329 dated Apr. 3, 2003.
Official Action corresponding to U.S. Appl. No. 09/700,402 dated Mar. 27, 2007.
Official Action corresponding to U.S. Appl. No. 09/700,402 dated Oct. 25, 2007.
Official Action corresponding to U.S. Appl. No. 10/235,236 dated Aug. 10, 2005.
Official Action corresponding to U.S. Appl. No. 10/323,692 dated Aug. 10, 2005.
Official Action corresponding to U.S. Appl. No. 10/829,137 dated Oct. 15, 2007.
Official Action corresponding to U.S. Appl. No. 12/221,956 dated Oct. 4, 2011.
Official Action corresponding to U.S. Appl. No. 13/012,433 dated Jul. 20, 2011.
Taetle et al., "Effects of combined antigrowth factor receptor treatment on in vitro growth of multiple myeloma," J. Natl. Cancer Inst. vol. 86, No. 6 pp. 450-455 (1994) [Abstract].
Tytgat et al., "Five-Year Cimetidine Maintenance Trial for Peptic Ulcer Disease," Scandinavian Journal of Gastroenterology. vol. 25, No. 10 pp. 974-980 (1990).
Watson et al., "A comparison of the therapeutic effectiveness of gastrin neutralization in two human gastric cancer models: relation to endocrine and autocrine/paracrine gastrin mediated growth," Gut. vol. 45 pp. 812-817 (1999).
Notice of Allowance corresponding to Canadian Patent Application No. 2,520,010 dated Nov. 22, 2011.
Official Action corresponding to Australian Patent Application No. 2005286164 dated Oct. 4, 2011.
"Clinical trial initiated with chemorefractory patients," Cancer Weekly, The Gale Group, (2001).
"Clinical trials update," Scrip, Informa UK Ltd., 2547:25, (2000).
"Gastrin 17 immunogen Aphton begins combination study," R & D Focus Drug News, IMS World Publications, (2000).
"Other news to note," Bioworld Today, American Health Consultants Inc., 11(82), (2000).
Aphton Biopharma BIO2005 Presentation, Jun. 19-22, Philadelphia, PA (2005), 26 pages.
Ardill et al., "Autoantibodies to gastrin in patients with pernicious anaemia—a novel antibody," QJ Med 91:739, 1998.
Ardis R&D Profile, "Gastrin 17 vaccine—Aphton: Anti-gastrin 17 immunogen, G17DT," Biodrugs 17(3):223-225 (2003).
Baldwin et al., "Binding of the progastrin fragments to the 78KDA gastrin-binding protein," FEBS Lett. 359:97-100 (1995).
Brett et al., "Lymphocyte expression of the CCK-B/gastrin receptor (CCK-BR) in gastric lymphomas, *Helicobacter pylori* gastritis and normal gastric biopsies," Gastroenterology 114:(Supplement 1):A570 (Abstract #G2333) (Apr. 15, 1998).
Caplin et al., "Demonstration of new sites of expression of the CCK-B/gastrin receptor in pancreatic acinar AR42J cells using immunoelectron microscopy," Regulatory Peptides 84(1-3):81-89 (1999).
Caplin et al., "Effect of gastrin and anti-gastrin antibodies on proliferation of hepatocyte cell lines," Digestive Diseases and Sciences 46(7):1356-1366 (2001).
Caplin et al., "Expression and processing of gastrin in hepatocellular carcinoma, fibromellar carcinoma and cholangiocarcinoma," Journal of Hepatology, 30(3):519-526, (1999).
Caplin et al., "Serum gastrin levels and identification of CCK-B-gastrin receptor following partial hepatectomy for liver tumours in man," Gastroenterology, 110(4 suppl.) A1162, (1996).
Caplin et al., "Expression and processing of gastrin in patients with hepatocellular carcinoma, fibrolamellar carcinoma and cholangiocarcinoma," Gastroenterology 114(Supplement 1): A1219 (Abstract # L0083) (Apr. 15, 1998).
Caplin et al., "Expression and processing of gastrin in patients with pancreatic carcinoma," Gastroenterology 114(Supplement 1): A445 (Abstract # G1809) (Apr. 15, 1998).

Del Valle et al., "Progastrin and its glycine-extended post-translational processing intermediates in human gastrointestinal tissues," Gastroenterology 92:1908-1912 (1987).
Gilliam et al., "A Phase II study of G17DT in gastric carcinoma," EJSO 30:536-543 (2004).
Gilliam et al., "G17DT: an antigastrin immunogen for the treatment of gastrointestinal malignancy," Expert Opin Biol Ther. 7(3):397-404 (2007).
Gilliam et al., "Randomised, double blind, placebo-controlled, multi-centre, group-sequential trial of G17DT for patients with advanced pancreatic cancer unsuitable or unwilling to take chemotherapy," J. Clin. Oncol. ASCO Annual Meeting Proceedings 22(14S):2511 (2004).
Hananel et al., "Hepatic resection for colorectal liver metastasis," Am. Surgeon 61(5):444-447 (1995).
Harris et al., "The biological and therapeutic importance of gastrin gene expression in pancreatic adenocarcinomas," Cancer Res. 64:5624-5631 (2004).
Harris et al., "An antiapoptotic role for gastrin and the gastrin/CCK-2 receptor in Barrett's esophagus," Cancer Res. 64(6):1915-1919 (2004).
Kaiser, "First pass at cancer genome reveals complex landscape," Science:313 1370 (2006).
Kothary et al., "NH2-terminal of gastrin-17 in duodenal ulcer disease:Identification of progastrin-17," Biochemical and Biophysical Research Communications 146(2):884-888 (1987).
Kothary et al., "Identification of gastrin molecular variants in gastrinoma syndrome," Regulatory Peptides 17:71-84 (1987).
Mu et al., "Monoclonal antibody to the gastrin receptor on parietal cells recognizes a 78-kDa protein," Proc. Natl. Acad. Sci. 84:2698-2702 (1987).
Nemeth et al., "Identification of progastrin derived peptides in colorectal carcinoma extracts," Gut 34:90-95 (1993).
Rahier et al., "Biosynthesis of gastrin. Localization of the precursor and peptide products using electron microscopic," Gastroenterology 92:1146-1152 (1987).
Rehfeld et al., "Gastrin in human bronchogenic carcinomas: constant expression but variable processing of progastrin," Cancer Res. 49:2840-2843 (1989).
Senior, K., "Immunization blocks gastrin's ability to promote tumour cell division" Drug Disc. Today 6(2):62-63 (2001).
Seva et al, "Growth-promoting effects of glycine-extended progastrin," Science 265:410-412 (1994).
Singh et al., "High levels of progastrin significantly increase premalignant changes in colonic mucosa of mice in response to the chemical carcinogen, AOM" Gastroenterology 114(4):A680 (1998).
Singh et al., "Incomplete processing of progastrin expressed by human colon cancer cells: roles of noncarboxyamidated gastrins," The American Physiological Society G459-G468 (1994).
Smith et al. "Gastrin regulates the growth of human pancreatic cancer in a tonic and autocrine fashion" Amer. J. Physiol. 270(5):R1078-R1084 (1996).
Smith et al., "Gastrin and gastrin receptor activation: an early event in the adenoma-carcinoma sequence," Gut 47(6):820-824 (2000).
Smith et al., "Gastrin may have an autocrine/paracrine role in Barrett's oesophagus and oesophageal adenocarcinoma," British Journal of Surgery 84:706-707, (1997).
Smith et al., "Phase I/II study of G17-DT, an anti-gastrin immunogen, in advanced colorectal cancer," Clinical Cancer Research 6(12):4719-4724, (2000).
Sobhani et al., "Immunohistochemical characterization of gastrinomas with antibodies specific to different fragments of progastrin," Gastroenterol. Clin. Biol. 13:865-872 (1989).
Stubbs et al., "Correlation between uptake of labelled anti-CCKB/gastrin receptor antibodies and the occurrence of apoptosis in hepatoma cell lines," Gastroenterology 122(4 Suppl. 1):A-380 (2002).
Stubbs et al., "Endocytosis of anti-CCK-B/Gastrin receptor antibody and effect on hepatoma cell lines," J. Histochemistry Cytochemistry 50(9):1213-1217 (2002).

Sugano, et al. "Identification and characterization of glycine-extended post translational processing intermediates of progastrin in porcine stomach," J. of Biological Chemistry 260:11724-11729 (1985).

Todisco et al., "Gastrin and glycine-extended progastrin processing intermediates induce different programs of early gene activation," J. Biol. Chem. 279:28337-28341 (1995).

Van-Solinge et al., "Expression but incomplete maturation of progastrin in colorectal carcinomas," Gastroenterology 104:1099-1107 (1993).

Varro et al., "Discrimination between Temperature- and Brefeldin A—sensitive Steps in the Sulfation, Phosphorylation, and Cleavage of Progastrin and its Derivatives," J. Biol. Chem. 269(32): 20764-20770 (1994).

Varro et al., "Gastrin: an analytical review," Ann. Clin. Biochem. 40:472-480 (2003).

Varro et al., "Pathways of processing of the gastrin precursor in rat antral mucosa," J. Clin. Invest. 95:1642-1649 (1995).

Varro et al., "Post-translational processing of progastrin: inhibition of cleavage, phosphorylation and sulphation by brefeldin A," Biochem J. 295:813-819 (1993).

Varro et al., "The Human Gastrin Precursor," Biochem J. 256:951-957 (1988).

Wang et al., "Processing and proliferative effects of human progastrin in transgenic mice," J. Clin. Invest. 98(8):1918-1929 (1996).

Watson et al., "A comparison of an anti-gastrin antibody and cytotoxic drugs in the therapy of human gastric ascites in SCID mice," International Journal of Cancer 81(2):248-254 (1999).

Watson et al., "Antibodies raised by gastrimmune inhibit the spontaneous metastasis of a human colorectal tumour AP5LV," European Journal of Cancer 35(8):1286-1291 (1999).

Watson et al., "Anti-gastrin antibodies raised by gastrimmune inhibit growth of colorectaltumor AP5," Int. J. Cancer, 61(2):233-240 (1995).

Watson et al., "Antiserum raised against an epitope of the cholecystokinin B/gastrin receptor inhibits hepatic invasion of a human colon tumor," Cancer Research 60(20):5902-5907 (2000).

Watson et al., "Detection of gastrin receptors on gastrointestinal tumors using the anti-gastrin receptor monoclonal antibody, 2CL," Gut 4:F271 (1993).

Watson et al., "Enhanced inhibition of Pancreatic Cancer by Combination of the G17DT Immunogen and Gemcitabine" Amer. Soc. Clin. Oncol. Abstract 37 (2002).

Watson et al., "Expression of gastrin-CCKB receptor isoforms in gastrointestinal tumor cells," Int. J. Cancer 77(4):572-577 (1998).

Watson et al., "Expression of gastrin-CCKB receptor isoforms in gastrointestinal tumor cells: Relationship to gastrin secretion," Proceedings of the American Association for Cancer Research Annual Meeting, 38(0):116 (Abstract 773), (1997).

Watson et al., "Gastrimmune raises antibodies that neutralize amidated and glycine-extended gastrin-17 and inhibit the growth of colon cancer," Cancer Res. 56:880-885 (1996).

Watson et al., "Gastrin antagonists and gastrointestinal tumors," Expert Opinion on Investigational Drugs, 4(12):1253-1266 (1995).

Watson et al., "Gastrin antagonists in the treatment of gastric cancer," Anticancer Drugs 4(6):599-604 (1993).

Watson et al., "Gastrin inhibition increases the potency of cytotoxic agents in pancreatic cancer," Gastroenterology 122(4):A241 (Abstract M952) (2002).

Watson et al., "Gastrin Receptors in Gastrointestinal Tumors", Medical Intelligence Unit, R.G. Landes Company, Georgetown, TX. pp. 1-99, (1993).

Watson et al., "Hypergastrinemia promotes adenoma progression in the APCMin−/+ Mouse Model of Familial Adenomatous Polyposis," Cancer Research 61:625-631 (2001).

Watson et al., "Inhibition of gastrin-stimulated growth of gastrointestinal tumour cells by octreatide and the gastrin/cholecystokinin receptor antagonists, proglumide and lorglumide," European Journal of Cancer, 28A(8-9):1462-1467, (1992).

Watson et al., "Inhibitory effects of the gastrin receptor antagonist (L-365,260) on gastrointestinal tumor cells," Cancer 68:1255-1260, (1991).

Watson et al., "Intracellular gastrin in human gastrointestinal tumor cells," Journal of the National Cancer Institute 83:866-871 (1991).

Watson et al., "Pre-clinical evaluation of the Gastrimmune immunogen alone and in combination with 5-fluorouracil/leucovorin in a rat colorectal cancer model," Int. J. Cancer 75(6):873-877 (1998).

Watson et al., "Synergistic inhibitory effects of G17DT on gastrointestinal tumor growth in combination with cytotoxic agents," Proc. Am. Soc. Clin. Oncol. 22:2003 (abstr 3497) (2003).

Watson et al., "The effect of the E2 prostaglandin enprostil, and the somatostatin analogue sms201995, on the growth of a human gastric cell line, MKN45G" Int. J. Cancer 45:90-94 (1990).

Watson et al., "The in vitro growth response of primary human colorectal and gastric cancer cells to gastrin," International Journal of Cancer, 43:692-696, (1989).

Watson et al., "Therapeutic effect of the gastrin receptor antagonist, CR2093 on gastrointestinal tumour cell growth," British Journal of Cancer, 65(6):879-883, (1992).

Watson et al., "Antibodies targeting the amino terminal portion of the human CCKB/gastrin receptor inhibit the liver invasion of a human colonic tumor," Gastroenterology 114(4 Part 2):A701 (Abstract # G2899) (Apr. 15, 1998).

Watson et al., "Antibodies targeting the amino terminal portion of the human CCKB/gastrin receptor inhibit the liver invasion of a human colonic tumour," Research Presentation, Digestive Disease Week, American Gastroenterological Association (1998), 17 slides.

Watson et al., "Effect of gastrin neutralization on the progression of the adenoma:carcinoma sequence in the Min mouse model of familial adenomatous polyposis," Gastroenterology 114(Supplement 1):A701 (Abstract #G2900) (Apr. 15, 1998).

Watson et al., "Gastrin: growth promoting effects on human gastric and colonic tumour cells," Br. J. Cancer 59:554-558 (1989).

Watson, S.A. and A.D. Gilliam, "A new weapon in the therapeutic armoury for gastrointestinal malignancy," Expert Opinion on Biological Theory 1(2):309-317 (2001).

Watson, S.A., et al., "Gastrin: growth enhancing effects on human gastric and colonic tumour cells," British Journal of Surgery 75(4):342-345 (1988).

"ADAP drugs: leucovorin," Access Project, http://www.aegis.com/factshts/network/access/drugs/leuc.html (1996) (accessed on Aug. 13, 2004), 1 page.

"Development and Activity of 5-FU," CancerQuest, http://www.cancerquest.org/index.cfm?page=443 (accessed on Aug. 13, 2004) 1 pg.

"*Prilosec* OTC Review: Two Advisory Committee Members Weigh in Without Voting," The Pink Sheet. pp. 22-23 (2002).

Akai, "Co-Existence and Co-Release of Gastrin 34 *N*-Terminal Fragment With Gastrin 17 in Rat Stomach," Folla endocrinol. vol. 64 pp. 1065-1080 (1988) [Abstract].

Baba et al., "Glycine-Extended Gastrin Induces Matrix Metalloproteinase-1- and -3-Mediated Invasion of Human Colon Cancer Cells Through Type 1 Collagen Gel and Matrigel," International Journal of Cancer. vol. 111, No. 1 pp. 23-31 (2004).

Belani, C., "Paclitaxel and Docetaxel Combinations in Non-Small Cell Lung Cancer," Chest. vol. 117 pp. 144S-151S (2000).

Bentley et al., "Human Gastrin: Isolation, Structure and Synthesis," Nature. vol. 209, No. 5023 pp. 583-585 (1966).

Berg et al. in "Biochemistry," New York: W.H. Freeman and Co., 4.3.1-4.3.3 and Figure 4.35 (2002).

Bock et al., "Benzodiazepine Gastrin and Brain Cholecystokinin Receptor Ligands: L-365,260," Journal of Medicinal Chemistry. vol. 32, No. 1 pp. 13-16 (1989).

Bold et al., "Gastrin Stimulates Growth of Human Colon Cancer Cells Via a Receptor Other Than CCK-A or CCK-B," Biochemical and Biophysical Research Communications. vol. 202, No. 3 pp. 1222-1226 (1994).

Brett et al., "The Effect of Antibodies Raised Against Gastrimmune on the Proliferation of Human Pancreatic Carcinoma Cell Lines," Gut. vol. 42 p. A26 (1998) [Abstract # W190].

Brinton et al., "Cancer risk following pernicious anaemia," Br. J. Cancer. vol. 59, No. 5 pp. 810-813 (1989).

Bruns et al., "Therapy of Human Pancreatic Carcinoma Implants by Irinotecan and the Oral Immunomodulator JBT 3002 is Associated with Enhanced Expression of Inducible Nitric Oxide Synthase in Tumor-infiltrating Macrophages," Cancer Research. vol. 60 pp. 2-7 (2000).

Budavari et al., The Merck Index (11$^{th}$ ed.), Rahway, New Jersey, Merck & Co., p. 1082 (1989).

Burkitt et al., "Importance of gastrin in the pathogenesis and treatment of gastric tumors," World J. Gastroenterol. vol. 15, No. 1 pp. 1-16 (2009).

Caplin et al., "The CCK-B/Gastrin Receptor in Hepatocellular Carcinoma," Gastroenterology. vol. 110, No. 4 p. A1162 (1996) [Abstract].

Certificate of Patent corresponding to Japanese Patent Application No. 2006-509465 dated Feb. 25, 2011.

Certified English Translation of PCT Patent Application No. WO2001/13114, "Use of stabilized synthetic compounds in immunoassay." Publication date: Feb. 22, 2001.

de Weerth et al., "Human Pancreatic Cancer Cell Lines Express the CCKB Receptor," Hepato-Gastroenterology. vol. 46 pp. 472-478 (1999).

de Weerth et al., "Human Pancreatic Cancer Cell Lines Express the $CCK_B$/Gastrin Receptor," Gastroenterology. vol. 106, No. 4 p. A289 (1994) [Abstract].

Deed of Letters Patent corresponding to Australian Patent Application No. 2004225437 dated Aug. 26, 2010.

Dufresne et al., "Cholecystokinin and Gastrin Receptors," Physiol. Rev. vol. 86 pp. 805-847 (2006).

Edgington, "Biotech Vaccines' Problematic Promise," Bio/Technology. vol. 10 pp. 763-766 (1992).

Evans, "Chemotherapy in Advanced Non-Small Cell Lung Cancer," 37$^{th}$ Annual Meeting of the American Society of Clinical Oncology, Day 1, May 22, 2001, meeting report published by Medscape.

Fennerty, "Updated on Barrett's Esophagus" Digestive Diseases Week, May 22, 2001, meeting report published by Medscape, www.medscape.com, 6 pages.

Festen et al., "Effect of Oral Omeprazole on Serum Gastrin and Serum Pepsinogen I Levels," Gastroenterology. vol. 87, No. 5 pp. 1030-1034 (1984).

Fields, "Preparation of Antipeptide Antibodies: Introduction to Peptide Synthesis," Current Protocols in Molecular Biology. 11.15.1-11.15.9 (2002).

Fornai et al., "Cholecystokinin CCK2 receptors mediate the peptide's inhibitory actions on the contractile activity of human distal colon via the nitric oxide pathway," British Journal of Pharmacology. vol. 151 pp. 1246-1253 (2007).

Fraser, "Effects of Antibodies to Luteinizing Hormone Releasing Hormone on Reproductive Functions in Rodents," Immunization With Hormones in Reproduction Research. Nieschlag ed. North Holland Publishing. pp. 107-117 (1975).

Freston, "Long-Term Acid Control and Proton Pump Inhibitors: Interactions and Safety Issues in Perspective," American Journal of Gastroenterology. vol. 92, No. 4 pp. 51S-57S (1997).

Gil-Delgado et al., "Prospective Phase II Trial of Irinotecan, 5-Fluorouracil, and Leucovorin in Combinations as Salvage Therapy for Advanced Colorectal Cancer," American Journal of Clinical Oncology. vol. 24, No. 1 pp. 101-105 (2001).

Goetze, J.P., and Rehfeld, J.F., "Impact of Assay Epitope Specificity in Gastrinoma Diagnosis," Clinical Chemistry. vol. 49, No. 2 pp. 333-334 (2003).

Grabowska, A., and Watson, S.A., "Downregulation of the Gastrin Gene Using Small Interfering RNA," Regulatory Peptides. vol. 122, No. 1 p. 46 (2004) [Abstract # A150].

Gutman et al., "Accelerated Growth of Human Colon Cancer Cells in Nude Mice Undergoing Liver Regeneration," Invasion and Metastasis. vol. 14, Nos. 1-6 pp. 362-371 (1994-95).

Harlow, E., and Lane, D., Antibodies: A Laboratory Manual, Cold Spring Harbor Laboratory Press. Cold Spring Harbor, NY. pp. 7-13, 23-26, 142-143, 148-149 (1988).

Harlow E., and Lane, D., Antibodies: A Laboratory Manual. Cold Spring Harbor Laboratory Press. Cold Spring Harbor, NY. pp. 555-556, 559, 561, 578-581, and 591-593 (1988).

Harrison et al. "The Effect of the Gastrin Receptor Antagonist Proglumide on Survival in Gastric Carcinoma," Cancer. vol. 66, No. 7 pp. 1449-1452 (1990).

He et al., "Biological Activity and Ferric Ion Binding of Fragments of Glycine-Extended Gastrin," Biochemistry. vol. 43, No. 37 pp. 11853-11861 (2004).

Heinemann et al., "Cellular Elimination of 2',2'-Diflourodeoxyxytidine 5'-Triphosphate: A Mechanism of Self-Potentiation," Cancer Research. vol. 52 pp. 533-539 (1992).

Huang et al., "Termination of DNA Synthesis by 9-β-D-Arabinofuranosyl-2-fluroadenine," The Journal of Biological Chemistry. vol. 265, No. 27 pp. 16617-16625 (1990).

Ikeda et al., "Preliminary report of tumor metastasis during liver regeneration after hepatic resection in rats," European Journal of Surgical Oncology. vol. 21, No. 2 pp. 188-190 (1995).

International Preliminary Examination Report corresponding to International Patent Application No. PCT/US1999/010734 dated Dec. 9, 2000.

International Preliminary Examination Report corresponding to International Patent Application No. PCT/US2002/021768 dated Feb. 9, 2004.

International Preliminary Report on Patentability corresponding to International Patent Application No. PCT/US2005/010532 dated Nov. 3, 2006.

Issued Patent corresponding to Australian Patent Application No. 2005228897 dated Mar. 25, 2010.

Iwao et al., "Effects of Omeprazole and Lansoprazole on Fasting and Postprandial Serum Gastrin and Serum Pepsinogen A and C," Hepato-Gastroenterology. vol. 42 pp. 677-682 (1995).

Jaffe et al., "Inhibition of Endogenous Gastrin Activity by Antibodies to the Carboxyl-Terminal Tetrapeptide Amide of Gastrin," Gastroenterology. vol. 58, No. 2 pp. 151-156 (1970).

Justin et al., "Gastric Acid Suppression Using Anti-Gastrin-17 Antibodies Produced by a Gastrin Immunogen, Gastrimmune, in an In Vivo Pig Model," Gastroenterology. vol. 108, No. 4 p. A125 (1995) [Abstract].

Koelz, "Treatment of Reflux Esophagitis with H2-Blockers. Antacides and Prokinetic Drugs. An Analysis of Randomized Clinical Trials," Scandinavian Journal of Gastroenterology. Supplement 156 pp. 25-36 (1989).

Koh et al., "Gastrin Deficiency Results in Altered Gastric Differentiation and Decreased Colonic Proliferation in Mice," Gastroenterology. vol. 113, No. 3 pp. 1015-1025 (1997).

Koh et al., "Glycine-Extended Gastrin Promotes the Growth of a Human Hepatoma Cell Line," Gastroenterology. vol. 110, No. 4 p. A1089 (1996) [Abstract].

Koh et al., "Glycine-Extended Gastrin Promotes the Growth of Lung Cancer," Cancer Research. vol. 64 pp. 196-201 (2004).

Kohler et al., "Continuous cultures of fused cells secreting antibody of predefined specificity," Nature. vol. 256 pp. 495-497 (1975).

Kopin et al. "Expression, cloning and characterization of the canine parietal cell gastrin receptor," PNAS. vol. 89 pp. 3605-3609 (1992).

Kovacs et al., "Gastrin is a Major Mediator of the Gastric Phase of Acid Secretion in Dogs: Proof by Monoclonal Antibody Neutralization," Gastroenterology. vol. 97 pp. 1406-1413 (1989).

Kovacs et al., "Gastrin Partially Mediates Insulin-Induced Acid Secretion in Dogs," Peptides. vol. 17, No. 4 pp. 583-587 (1996).

Kovacs et al. "Inhibition of sham feeding-stimulated acid secretion in dogs by immunoneutralization of gastrin," Am. J. Physiol. vol. 273 (Gastrointest. Liver Physiol. 36) pp. G399-G403 (1997).

Kuipers et al., "Atrophic Gastritis and *Helicobacter pylori* Infecion in Patients with Reflux Esophagitis Treated with Omeprazole or Fundoplication," New England Journal of Medicine. vol. 334, No. 16 pp. 1018-1022 (1996).

Kuipers et al., "The Efficacy and Safety of Long-term Omeprazole Treatment for Gastroesophageal Reflux Disease," Gastroenterology. vol. 118, No. 4 pp. 795-798 (2000).

Kusyk et al., "Stimulation of growth of a colon cancer cell line by gastrin," Am. J. Physiol. vol. 251 pp. G597-G601 (1986).

Lamberts et al., "Effects of Very Long (up to 10 years) Proton Pump Blockade on Human Gastric Mucosa," Digestion. vol. 64 pp. 205-213 (2001).

Lamers, C.B.H.W., and Jansen, J.B.M.J., "Role of Gastrin and Cholecystokinin in Tumours of the Gastrointestinal Tract," Eur. J. Cancer Clin. Oncol. vol. 24, No. 2 pp. 267-273 (1988).

Lamote, J., and Willems, G., "Stimulating effect of pentagastrin on cancer cell proliferation kinetics in chemically induced colon cancer in rats," Regulatory Peptides. vol. 20 pp. 1-9 (1988).

Larsson, "Histochemistry of Gastrin Cells," Neurohistochemistry: Modern Methods and Applications. Alan R. Liss, Inc., pp. 527-567 (1986).

Larsson, L., and Rehfeld, J.F., "Characterization of Antral Gastrin Cells With Region-Specific Antisera," The Journal of Histochemistry and Cytochemistry. vol. 25, No. 12 pp. 1317-1321 (1977).

Laurie, S.A., and Kris, M.G., "Single-Agent Docetaxel (Taxotere) in the Treatment of Advanced Non-Small-Cell Lung Cancer: Clinical Concepts and Commentary," Clinical Lung Cancer. vol. 1, Suppl 1 pp. S5-S9 (2000).

Lawrence et al., "Radiosensitization of Pancreatic Cancer Cells by 2', 2'-Difluoro-2'-Deoxycytidine," Int. J. Radiation Oncology Biol. Phys. vol. 34, No. 4 pp. 867-872 (1996).

Le Meuth et al., "Differential Expression of A- and B-Subtypes of Cholecystokinin/Gastrin-Receptors in the Developing Calf Pancreas," Endocrinology. vol. 133, No. 3 pp. 1182-1191 (1993).

Ledda-Columbano et al., "Compensatory Regeneration, Mitogen-Induced Liver Growth, and Multistage Chemical Carcinogenesis," Environmental Health Perspectives. vol. 101, No. 5 pp. 163-168 (1993).

Lee et al., "The Human Brain Cholecystokinin-B/Gastrin Receptor," The Journal of Biological Chemistry. vol. 268, No. 11 pp. 8164-8169 (1993).

Leith et al., "Effects of Partial Hepatectomy on Growth Characteristics and Hypoxic Fractions of Xenografted DLD-2 Human Colon Cancers," Radiation Research. vol. 123, No. 2 pp. 263-268 (1992).

Li et al., "Induction of growth inhibition and apoptosis in pancreatic cancer cells by auristatin-PE and gemcitabine," International Journal of Molecular Medicine. vol. 3 pp. 647-653 (1999).

Machine translation of JP 06107564, 2010.

MacKenzie et al., "Development of a Radioligand Binding Assay to Characterise Gastrin Receptors in the Human Gastrointestinal Tract," Gut. vol. 38, Suppl. 1 p. A37 (1996) [Abstract #T146].

Mahood et al., "Inhibition of Fluorouracil Stomatitis by Oral Cryotherapy," Journal of Clinical Oncology. vol. 9 pp. 449-452 (1991).

Makishima et al., "Active Immunication Against Gastrin-17 With an N-Terminal Derived Immunogen Inhibits Gastric and Duodenal Lesions in Rats," Gastronenterology. vol. 106, No. 4, Part. 2 p. A824 (1994) [Abstract].

Makishima et al., "Inhibition of Gastrin-17 Stimulated Acid Secretion Through Active Immunization in Rats," FASEB Journal. vol. 8, Nos. 4-5 p. A92 (1994) [Abstract #535].

Mandair et al., "Cholecystokinin Receptors in Human Pancreatic Cancer Cell Lines," European Journal of Cancer. vol. 34, No. 9 pp. 1455-1459 (1998).

Marino et al., "Expression and Post-translational Processing of Gastrin in Heterologous Endocrine Cells," The Journal of Biological Chemistry. vol. 266, No. 10 pp. 6133-6136 (1991).

Martin et al. "Selection of Trypsin of 2 Sublines of Rat Cancer Cells Forming Progressive or Regressive Tumors," Int. J. Cancer. vol. 32 pp. 623-627 (1983).

Masseyeff, R.F., and Ferrua, B., "The Art of Assay Design in Heterologous Enzyme Immunoassay," International symposium on immunoenzymatic techniques. vol. 2 pp. 139-155 (1983).

Matsumoto et al. "Gastrin receptor characterization: affinity cross-linking of the gastrin receptor on canine gastric parietal cells," Am J. Physiol. vol. 252 p. G143-G147 (1987).

McCloy et al., "Pathophysiological Effects of Long-Term Acid Suppression in Man," Digestive Diseases and Sciences. vol. 40, No. 2 pp. 96S-120S [Supplement] (1995).

McGregor et al., "Trophic Effects of Gastrin on Colorectal Neoplasms in the Rat," Ann. Surg. vol. 195, No. 2 pp. 219-223 (1982).

McRae et al., "Role of Gastrin and Gastrin Receptors in the Growth of Human Colon Carcinoma Cells," The Journal of Cell Biology. vol. 103, No. 5, Part 2 p. 22a (1986) [Abstract # 74].

McWilliams et al., "Antibodies raised against the extracellular tail of the CCKB/gastrin receptor inhibit gastrin-stimulated signalling," Regulatory Peptides. vol. 99, Nos. 2-3 pp. 157-161 (2001).

McWilliams et al., "Coexpression of gastrin and gastrin-receptors (CCK-B and CCK-B) in gastrointestinal tumour cell lines," Gut. vol. 42 pp. 795-798 (1998).

Miyake, "A Truncated Isoform of Human CCK-B/Gastrin Receptor Generated by Alternative Usage of a Novel Exon," Biochemical and Biohysical Research Communications. vol. 208, No. 1 pp. 230-237 (1995).

Mizutani et al., "Promotion of hepatic metastases by liver resection in the rat," British J. Cancer. vol. 65, No. 6 pp. 794-797 (1992).

Moertel, C.G., "Chemotherapy for Colorectal Cancer," The New England Journal of Medicine. vol. 330, No. 16 pp. 1136-1142 (1994).

Moody et al., "GRP Receptors Are Present in Non Small Cell Lung Cancer Cells," Journal of Cellular Biochemistry Supplement. vol. 24 pp. 247-256 (1996).

Moroder, L., and Wunsch, E., "Gastrins and Cholecystokinins: Chemical and Immunological Aspects," Gastrin and Cholecystokinin. Chemistry, physiology and pharmacology. (Ed. J. Bali et al.) Elsevier Science Publishers B.V. pp. 21-32 (1987).

MSNBC News Services, "Mixed results on new cancer drug," Nov. 9, 2000 (4 pages).

Mulholland et al., "Elevated Gastric Acid Secretion in Patients with Barrett's Metaplastic Epithelium," Digestive Diseases and Sciences. vol. 34, No. 9 pp. 1329-1334 (1989).

Nakata et al., "Cloning and Characterization of Gastrin Receptor From ECL Carcinoid Tumor of Mastomys Natalensis," Biochemical and Biophysical Research Communications. vol. 187, No. 2 pp. 1151-1157 (1992).

Narayan et al., "Characterization of gastrin binding to colonic mucosal membranes of guinea pigs," Molecular and Cellular Biochemistry. vol. 112 pp. 163-171 (1992).

National Institutes of Health Publication No. 99-4546, "Barrett's Esophagus," National Digestive Diseases Information Clearinghouse. pp. 1-3 (May 1999).

NCBI Accession No. NP 795344. Fornai et al., "Cholecystokinin CCK2 receptors mediate the peptide's inhibitory actions on the contractile activity of human distal colon via the nitric oxide pathway," British Journal of Pharmacology. vol. 151, No. 8 pp. 1246-1253 (2007).

Negre et al., "Autocrine Stimulation of AR4-2J Rat Pancreatic Tumor Cell Growth by Glycine-Extended Gastrin," Int. J. Cancer. vol. 66, No. 5 pp. 653-658 (1996).

Nemeth et al., "A Gasztrin Aminoterminalis 1-13 Fragmensével Kidolgozott, Szekvenciaspecifikus Radioimmunoassay," Izotoptechnika. vol. 25, No. 4 pp. 288-294 (1982) [Abstract].

Nemeth et al., "Development of a sequence-specific radioimmunoassay by using N-terminal gastrin 1-13 antibody," Chemical Abstracts. vol. 98 p. 495 (1983) [Abstract #98:51653w].

Notice of Acceptance corresponding to Australian Patent Application No. 2004225437 dated Apr. 29, 2010.

Notice of Acceptance corresponding to Australian Patent Application No. 2005228897 dated Nov. 25, 2009.

Notice of Allowance corresponding to Japanese Patent Application No. 2006-509465 dated Jan. 18, 2011.

Notice of Allowance corresponding to U.S. Appl. No. 10/813,336 dated May 15, 2006.

Notice of Allowance corresponding to U.S. Appl. No. 10/813,336 dated Oct. 3, 2006.

Notice of Allowance corresponding to U.S. Appl. No. 10/813,336 dated Feb. 7, 2007.

Notice of Allowance corresponding to U.S. Appl. No. 11/800,889 dated Feb. 7, 2011.

Ochiai et,al., "Growth-Promoting Effect of Gastrin on Human Gastric Carcinoma Cell Line TMK-1," Japan Journal of Cancer Research. vol. 76 pp. 1064-1071 (1985).

Official Action Corresponding to Australian Patent Application No. 199940798 dated Jul. 13, 2001.

Official Action corresponding to Australian Patent Application No. 199940798 dated Jul. 24, 2003.

Official Action corresponding to Australian Patent Application No. 2004225437 dated Dec. 15, 2009.

Official Action corresponding to Canadian Patent Application No. 2,520,010 dated Aug. 17, 2009.

Official Action corresponding to Canadian Patent Application No. 2,520,010 dated Nov. 1, 2010.
Official Action corresponding to Canadian Patent Application No. 2,450,898 dated May 28, 2010.
Official Action corresponding to Canadian Patent Application No. 2,561,405 dated Jul. 31, 2009.
Official Action corresponding to Canadian Patent Application No. 2,561,405 dated Nov. 3, 2010.
Official Action corresponding to Canadian Patent Application No. 2,580,965 dated Sep. 30, 2010.
Official Action corresponding to Chinese Patent Application No. 200580017341.9 dated Jun. 19, 2009.
Official Action corresponding to Chinese Patent Application No. 200580036710.9 dated Feb. 24, 2011.
Official Action corresponding to European Patent Application No. 02 721 529.2-2107 dated Sep. 23, 2004.
Official Action corresponding to European Patent Application No. 04 758 568.2-2404 dated Jul. 17, 2007.
Official Action corresponding to European Patent Application No. 05 730 336.4-1222 dated Apr. 27, 2007.
Official Action corresponding to European Patent Application No. 05 784 499.5-2406 dated Jul. 8, 2010.
Official Action corresponding to European Patent Application No. 99 924 252.2-2107 dated Jul. 4, 2003.
Official Action corresponding to European Patent Application No. 99 924 252.2-2107 dated Mar. 31, 2004.
Official Action corresponding to Indian Patent Application No. 2441/CHENP/2005 dated Jul. 24, 2007.
Official Action corresponding to Indian Patent Application No. 6318/DELNP/2006/707 dated Jul. 5, 2010.
Official Action corresponding to Israeli Patent Application No. 182012 dated Dec. 31, 2009.
Official Action corresponding to Japanese Patent Application No. 2006-509465 dated Oct. 21, 2009.
Official Action corresponding to Japanese Patent Application No. 2006-509465 dated Aug. 26, 2010.
Official Action corresponding to Japanese Patent Application No. 2007-506474 dated Jun. 1, 2010.
Official Action corresponding to U.S. Appl. No. 08/219,773 dated Oct. 19, 1994.
Official Action corresponding to U.S. Appl. No. 08/285,984 dated Feb. 7, 1995.
Official Action corresponding to U.S. Appl. No. 08/465,917 dated Aug. 12, 1996.
Official Action corresponding to U.S. Appl. No. 10/104,607 dated Mar. 29, 2005.
Official Action corresponding to U.S. Appl. No. 10/104,607 dated Nov. 21, 2005.
Official Action corresponding to U.S. Appl. No. 10/192,257 dated Sep. 21, 2005.
Official Action corresponding to U.S. Appl. No. 10/762,226 dated Dec. 27, 2006.
Official Action corresponding to U.S. Appl. No. 10/813,336 dated Jun. 23, 2005.
Official Action corresponding to U.S. Appl. No. 11/093,724 dated Nov. 25, 2005.
Official Action corresponding to U.S. Appl. No. 11/252,904 dated Jan. 8, 2009.
Official Action corresponding to U.S. Appl. No. 11/252,904 dated Oct. 26, 2009.
Official Action corresponding to U.S. Appl. No. 11/252,904 dated Jul. 20, 2010.
Official Action corresponding to U.S. Appl. No. 11/499,261 dated Mar. 15, 2007.
Official Action corresponding to U.S. Appl. No. 11/499,261 dated Nov. 30, 2007.
Official Action corresponding to U.S. Appl. No. 11/499,261 dated Sep. 24, 2008.
Official Action corresponding to U.S. Appl. No. 11/499,261 dated May 14, 2009.
Official Action corresponding to U.S. Appl. No. 11/499,261 dated Nov. 15, 2010.
Official Action corresponding to U.S. Appl. No. 11/800,889 dated Oct. 2, 2009.
Official Action corresponding to U.S. Appl. No. 11/800,889 dated Feb. 18, 2010.
Official Action corresponding to U.S. Appl. No. 11/800,889 dated Jun. 23, 2010.
Official Action corresponding to U.S. Appl. No. 12/221,956 dated May 28, 2010.
Official Action corresponding to U.S. Appl. No. 12/221,956 dated Feb. 16, 2011.
Official Action corresponding to U.S. Appl. No. 12/693,127 dated Jul. 16, 2010.
Official Action corresponding to U.S. Appl. No. 12/693,127 dated Feb. 11, 2011.
Ohkura et al., "Gastrin-Enhanced Tumor Growth of a Xenotransplantable Human Gastric Carcinoma in Nude Mice," Jpn. J. Clin. Oncol. vol. 10, No. 2 pp. 255-263 (1980).
Ohning et al., "Differential Kinetics for Immunoneutralization of Circulating Gastrin by Gastrin Monoclonal Antibody and its $Fab_1$ Fragment in Rats," Peptides. vol. 15 pp. 417-423 (1994).
Ohning et al., "Gastrin mediates the gastric mucosal proliferative response to feeding," American Journal of Physiology. vol. 271 (Gastrointest. Liver Physiol. 34) pp. G470-G476 (1996).
Ohsawa et al., "Effects of Three $H_2$-Receptor Antagonists (Cimetidine, Famotidine, Ranitidine) on Serum Gastrin Level," International Journal of Clinical Pharmacology Research. vol. 22, No. 2 pp. 29-35 (2002).
Ohtsu et al., "Randomized Phase III Trial of Fluorouracil Alone Versus Fluorouracil Plus Cisplatin Versus Uracil and Tegafur Plus Mitomycin in Patients With Unresectable, Advanced Gastric Cancer: The Japan Clinical Oncology Group Study (JCOG9205)," Journal of Clinical Investigation. vol. 21, No. 1 pp. 54-59 (2003).
Okada et al., "Evaluation of cholecystokinin, gastrin, CCK-A receptor, and CCK-B/gastrin receptor gene expressions in gastrin cancer," Cancer Letters. vol. 106, No. 2 pp. 257-262 (1996).
Osband, M.E., and Ross, S., "Problems in the investigational study and clinical use of cancer immunotherapy," Immunology Today. vol. 1, No. 6 pp. 193-195 (1990).
Palnæs Hansen et al., "Metabolism and Influence of Glycine-Extended Gastrin on Gastric Acid Secretion in Man," Digestion. vol. 57 pp. 22-29 (1996).
Pannequin et al., "Divergent roles for ferric ions in the biological activity of amidated and non-amidated gastrins," Journal of Endocrinology. vol. 181, No. 2 pp. 315-325 (2004).
Parsonnet et al., "*Helicobacter pylori* Infection and the Risk of Gastric Carcinoma," The New England Journal of Medicine. vol. 325, No. 16 pp. 1127-1131 (1991).
Pawlikowski et al., "Gastrin and Somatostatin Levels in Patients with Gastric Cancer," Horm. Metabol. Res. vol. 21 pp. 89-91 (1989).
Petrelli et al., "The Modulation of Fluorouracil With Leucovorin in Metastatic Colorectal Carcinoma: A Prospective Randomized Phase III Trial," Journal of Clinical Oncology. vol. 7 pp. 1419-1426 (1989).
Petrioli et al., "Treatment of Advanced Colorectal Cancer with High-dose Intensity Folinic Acid and 5-Fluorouracil Plus Supportive Care," European Journal of Cancer. vol. 31A, No. 12 pp. 2105-2108 (1995).
Podlecki et al., "Nuclear Translocation of the Insulin Receptor: A Possible Mediator of Insulin's Long Term Effects," The Journal of Biological Chemistry. vol. 262, No. 7 pp. 3362-3368 (1987).
Power et al., "A novel gastrin-processing pathway in mammalian antrum," Chemical Abstracts. vol. 109, No. 9 p. 113 (1988) [Abstract # 109:67341z].
Rae-Venter et al., "Gastrin Receptors in Human Colon Carcinoma," Gastroenterology. vol. 80, No. 5, Part 2 p. 1256 (1981) [Abstract].
Reddy, "Small Cell Lung Cancer: Improving Outcomes," American Society for Therapeutic Radiology and Oncology, 42nd Annual Meeting, Day 1, Oct. 22, 2000, meeting report published by Medscape.
Redmond, E.J., and Wetscher, G.J., "Gastroesophageal Reflux Disease," Ronald Hinder ed., R.G. Landes Company. pp. 1-6 (1993).
Rehfeld, "The New Biology of Gastrointestinal Hormones," Physiological Reviews. vol. 78, No. 4 pp. 1087-1108 (1998).

Rehfeld, J.F., "Gastrin and Colorectal Cancer: A Never-Ending Dispute?" Gastroenterology. vol. 108, No. 4 pp. 1307-1310 (1995).

Rehfeld, J.F., "Three Components of Gastrin in Human Serum," Biochimica et Biophysica Acta. vol. 285 pp. 364-372 (1972).

Rehfeld et al., "Cell-specific processing of pro-cholecystokinin and pro-gastrin," Biochimie. vol. 70 pp. 25-31 (1988).

Rehfeld et al., "Production and Evaluation of Antibodies for the Radioimmunoassay of Gastrin," Scnad. J. Clin. Lab. Invest. vol. 30 pp. 221-232 (1972).

Rehfeld, J.F., and Johnsen, A.H., "Residue-specific immunochemical sequence prediction," Journal of Immunological Methods. vol. 171 pp. 139-142 (1994).

Rehfeld et al., "Sulfation of Gastrin: Effect on Immunoreactivity," Regulatory Peptides. vol. 2 pp. 333-342 (1981).

Ritter et al., "Serological Analysis of Human Anti-Human Antibody Responses in Colon Cancer Patients Treated with Repeated Doses of Humanized Monoclonal Antibody A33," Cancer Research. vol. 61 pp. 6851-6859 (2001).

Robertson et al., "Effect of Gastrointestinal Hormones and Synthetic Analogues on the Growth of Pancreatic Cancer," Int. J. Cancer. vol. 63 pp. 69-75 (1995).

Rodriguez-Lescure et al., "Phase II Study of Gemcitabine (GEM) and Weekly 48-Hour Continuous Infusion (CI) with High Dose 5-Fluorouracil (5-FU) in Advanced Exocrine Pancreatic Cancer (APC)," Proceedings of the Annual Meeting of the American Society of Clinical Oncology. vol. 18, p. 298 (1999) [Abstract # 1145].

Romani et al. "Gastrin Receptor Antagonist CI-988 Inhibits Growth of Human Colon Cancer In Vivo and In Vitro," Aust. N.Z. J. Surgery. vol. 66 pp. 235-237 (1996).

Romani et al., "Potent new family of gastrin receptor antagonists (GRAs) produces in vitro and in vivo inhibition of human colorectal cancer (CRC) cell lines," Proceedings of the American Association for Cancer Research. vol. 35 p. 397 (1994) [Abstract # 2369].

Rothenberg et al., "A phase II trial of gemcitabine in patients with 5-FU-refractory pancreas cancer," Annals of Oncology. vol. 7 pp. 347-353 (1996).

Scemama et al., "Characterisation of gastrin receptors on a rat pancreatic acinar cell line (AR42J). A possible model for studying gastrin mediated cell growth and proliferation," Gut. vol. 28, No. S1 pp. 233-236 (1987).

Scheele et al., "Indicators of prognosis after hepatic resection for colorectal secondaries," Surgery. vol. 110, No. 1 pp. 13-29 (1991).

Scheithauer et al., "Combined Intraperitoneal plus Intravenous Chemotherapy after Curative Resection for Colonic Adenocarcinome," European Journal of Cancer. vol. 31A, No. 12 pp. 1981-1986 (1995).

Schlom, "Monoclonal Antibodies: They're More and Less Than You Think," Molecular Foundations of Oncology. ed. Broder Williams & Williams, Baltimore MD, pp. 95-134 (1991).

Schmitz et al., "CCK-B/gastrin receptors in human colorectal cancer," European Journal of Clinical Investigation. vol. 31 pp. 812-820 (2001).

Seitz et al., "Elevated Serum Gastrin Levels in Patients with Colorectal Neoplasia," J. Clin. Gastroenterol. vol. 13, No. 5 pp. 541-545 (1991).

Seva et al., "Characterization of the Glycine-Extended Gastrin (G-GLY) Receptor on AR4-2J Cells," Gastroenterology. vol. 108 p. A1005 (1995) [Abstract].

Seva et al., "Lorglumide and Loxglumide Inhibit Gastrin-stimulated DNA Synthesis in a Rat Tumoral Acinar Pancreatic Cell Line (AR42J)," Cancer Research. vol. 50, No. 8 pp. 5829-5833 (1990).

Shewach, D.S., and Lawrence, T.S., "Radiosensitization of Human Solid Tumor Cell Lines With Gemcitabine," Seminars in Oncology. vol. 23, No. 5, Suppl. 10 pp. 65-71 (1996).

Shewach et al., "Metabolism of 2',2'-Difluoro-2'-Deoxycytidine and Radiation Sensitization of Human Colon Carcinoma Cells," Cancer Research. vol. 54 pp. 3218-3223 (1994).

Siemann, "Satisfactory and Unsatisfactory Tumor Models: Factors Influencing the Selection of a Tumor Model for Experimental Evaluation," Rodent Tumor Models in Experimental Cancer Therapy (Ed. Kallman) Pergamin Press, NY. pp. 12-15 (1987).

Singh et al., "Novel Gastrin Receptors Mediate Mitogenic Effects of Gastrin and Processing Intermediates of Gastrin on Swiss 3T3 Fibroblasts. Absence of Detectable Cholecystokinin (CCK)-A and CCK-B Receptors," The Journal of Biological Chemistry. vol. 270, No. 15 pp. 8429-8438 (1995).

Singh et al., "Role of Gastrin and Gastrin Receptors on the Growth of a Transplantable Mouse Colon Carcinoma (MC-26) in BALB/c Mice," Cancer Research. vol. 46 pp. 1612-1616 (1986).

Singh et al., "Gut hormones in colon cancer: past and prospective studies," Cancer Journal. vol. 3, No. 1 pp. 28-33 (1990).

Sipponen et al., "Serum Levels of Amidated Gastrin-17 and Pepsinogen I in Atrophic Gastritis: An Observational Case-Control Study," Scandinavian Journal of Gastroenterology. vol. 37, No. 7 pp. 785-791 (2002).

Slooter et al., "Tumor growth stimulation after partial hepatectomy can be reduced by treatment with tumor necrosis factor α," British Journal of Surgery. vol. 82 pp. 129-132 (1995).

Smith, A.M., and Watson S.A., "Review Article: Gastrin and Colorectal Cancer," Alimentary Pharmacology & Therapeutics. vol. 14, No. 10 pp. 1231-1247 (2000).

Smith, J.P., and Solomon, T.E., "Effects of Gastrin, Proglumide, and Somatostatin on Growth of Human Colon Cancer," Gastroenterology. vol. 95, No. 6 pp. 1541-1548 (1988).

Smith et al., "Antisense oligonucleotides to gastrin inhibit growth of human pancreatic cancer," Cancer Letters. vol. 135 pp. 107-112 (1999).

Smith et al., "Characterization of the CCK-C (cancer) receptor in human pancreatic cancer," International Journal of Molecular Medicine. vol. 10, No. 6 pp. 689-694 (2002).

Smith et al., "Elevated Gastrin Levels in Patients with Colon Cancer or Adenomatous Polyps," Digestive Diseases and Science. vol. 34, No. 2 pp. 171-174 (1989).

Smith et al., "Gastric carcinoid expresses the gastrin autocrine pathway," British Journal of Surgery. vol. 85 pp. 1285-1289 (1998).

Smith et al., "Identification of gastrin as a growth peptide in human pancreatic cancer," American Journal of Physiology. vol. 268 (Regulatory Integrative Comp. Physiol. 37) pp. R135-R141 (1995).

Smith et al., "Sensitivity of the Esophageal Mucosa to pH in Gastroesophageal Reflux Disease," Gastroenterology. vol. 96 pp. 683-689 (1989).

Sobhani et al., "Chronic Endogenous Hypergastrinemia in Humans: Evidence for a Mitogenic Effect on the Colonic Mucosa," Gastroenterology. vol. 105, No. 1 pp. 22-30 (1993).

Soll et al. "Gastrin-Receptors on Isolated Canine Parietal Cells," The Journal of Clinical Investigation, Inc.. vol. 73 pp. 1434-1447 (1984).

Song et al., "The human gastrin/cholecystokinin type B receptor-gene: Alternative splice donor site in exon 4 generates two variant mRNAs," PNAS. vol. 90, No. 19 pp. 9085-9089 (1993).

Spitler, L.E. "Cancer Vaccines: The Interferon Analogy," Cancer Biotherapy. vol. 10, No. 1 pp. 1-3 (1995).

Stepan et al., "Glycine-Extended Gastrin Exerts Growth-Promoting Effects on Colon Cancer Cell Lines," Gastroenterology. vol. 110, No. 4 p. A1122 (1996) [Abstract].

Stepan et al., "Glycine-Extended Gastrin Exerts Growth-Promoting Effects on Human Colon Cancer Cells," Molecular Medicine. vol. 5, No. 3 pp. 147-159 (1999).

Sundler et al., "The Neuroendocrine System of the Gut—An Update," Acta Oncologica. vol. 30, No. 4 pp. 419-427 (1991).

Takhar et al., "The role of gastrin in colorectal carcinogenesis," J.R. Coll. Surg. Edinb. Irel. vol. 2, No. 5 pp. 251-257 (2004).

Takinami et al., "YF476 is a new potent and selective gastrin/cholecystokinin-B receptor antagonist in vitro and in vivo," Ailment Pharmacol. Ther. vol. 11, No. 1 pp. 113-120 (1997).

Talley et al., "Risk for Colorectal Adenocarcinoma in Pernicious Anemia," Annals of Internal Medicine. vol. 111, No. 9 pp. 738-742 (1989).

Tang et al., "Expression of receptors for gut peptides in human pancreatic adenocarcinoma and tumor-free pancreas," British Journal of Cancer. vol. 75, No. 10 pp. 1467-1473 (1997).

Taniguchi et al., "Cholecystokinin-B/gastrin receptor signaling pathway involves tyrosine phosphorylations of p125FAK and p42MAP," Oncogene. vol. 9 pp. 861-867 (1994).

Tarasova et al., "Anti-peptide antibodies specific for the gastrin/cholecystokinin-B receptor," Letters in Peptide Science. vol. 1 pp. 221-228 (1994).

Tarasova et al., "Endocytosis of gastrin in cancer cells expressing gastrin/CCK-B receptor," Cell and Tissue Research. vol. 287 pp. 325-330 (1997).

Taylor, "Chemotherapy, radiotherapy and immunotherapy of colorectal neoplasia," Current Opinion in Gastroenterology. vol. 9 pp. 28-33 (1993).

Thorndyke, M., and Dockray, G.J., "Identification and localization of material with gastrin-like immunoreactivity in the neutral ganglion of a photochordate, *Ciona intestinalis*," Regulatroy Peptides. vol. 16 pp. 269-279 (1986).

Tielemans et al., "Proliferation of Enterochromaffinlike Cells in Omeprazole-Treated Hypergastrinemic Rats," Gastrienterology. vol. 96, No. 3 pp. 723-729 (1989).

Torosian et al., "Colon Carcinoma Metastatic to the Thigh—An Unusual Site of Metastasis. Report of a Case," Diseases of the Colon and Rectum. vol. 30, No. 10 pp. 805-808 (1987).

Trakal et al., "Diagnosis and Etiology of Barrett's Esophagus: Presence of Gastrin Secreting Cells," Acta Gastroenterológica Latinoamericana. vol. 15, No. 2 pp. 67-80 (1985) [Abstract].

Tschmelitsch et al., "Enhanced Antitumor Activity of Combination Radioimmunotherapy ($^{131}$I-labeled Monoclonal Antibody A33) with Chemotherapy (Fluorouracil)," Cancer Research. vol. 57 pp. 2181-2186 (1997).

Ullrich et al. "Signal Transduction by receptors with Tyrosine Kinase Activity," Cell. vol. 61 pp. 203-212 (1990).

UniProtKB/Swiss-Prot entry P01350, (1986) (accessed on Mar. 26, 2007).

Upp et al., "Clinical Significance of Gastrin Receptors in Human Colon Cancers" Cancer Research. vol. 49 pp. 488-492 (1989).

Upp et al., "Polyamine Levels and Gastrin Receptors in Colon Cancers" Ann. Surg. vol. 207, No. 6 pp. 662-668 (1988).

Vaillant et al., "Cellular Origins of Different Forms of Gastrin. The Specific Immunocytochemical Localization of Related Peptides," The Journal of Histochemistry and Cytochemistry. vol. 27, No. 5 pp. 932-935 (1979).

Vaillant et al., "Repeat liver resection for recurrent colorectal metastasis," British J. Surgery. vol. 80, No. 3 pp. 340-344 (1993).

Van Cutsem et al., "Phase III Study of Docetaxel and Cisplatin Plus Fluorouracil Compared With Cisplatin and Fluorouracil as First-Line Therapy for Advanced Gastric Cancer: A Report of the V325 Study Group," Journal of Clinical Oncology. vol. 24, No. 31 pp. 4991-4997 (2006).

Vanhoefer et al., "Final Results of a Randomized Phase III Trial of Sequential High-Dose Methotrexate, Fluorouracil, and Doxorubicin Versus Etoposide, Leucovorin, and Fluorouracil Versus Infusional Fluorouracil and Cisplatin in Advanced Gastric Cancer: A Trial of the European Organization for Research and Treatment of Cancer Gastrointestinal Tract Cancer Cooperative Group," Journal of Clinical Oncology. vol. 18, No. 14 pp. 2648-2657 (2000).

Varndell et al., "Intracellular topography of immunoreactive gastrin demonstrated using electron immunocytochemistry," Experienta. vol. 39 pp. 713-717 (1983).

Vauthey et al., "Factors Affecting Long-Term Outcome After Hepatic Resection for Hepatocellular Carcinoma," The American Journal of Surgery. vol. 169 pp. 28-35 (1995).

Von Hoff, D.D., and Bearss, D., "New drugs for patients with pancreatic cancer," Curr. Opin. Oncology. vol. 14 pp. 621-627 (2002).

Wank, "Cholecystokinin receptors," Am. J. Physiol. vol. 269 (Gastrointest. Liver Physiol.) pp. G628-G646 (1995).

Wank et al., "Brain and gastrointestinal cholecystokinin receptor family: Structure and functional expression," PNAS. vol. 89 pp. 8691-8695 (1992).

Wank et al., "Cholecystokinin Receptor Family. Molecular Cloning, Structure, and Functional Expression in Rat, Guinea Pig, and Human," Annals New York Academy of Sciences. vol. 713 pp. 49-66 (1994).

Watson et al., "Gastrin: growth enhancing effects on human gastric and colonic tumour cells," British Journal of Surgery. vol. 75, No. 4 pp. 554-558 (1988).

Watson et al., "Growth-promoting action of gastrin on human colonic and gastric tumour cells cultured in vitro," British Journal of Surgery. vol. 75, No. 4 pp. 342-345 (1988).

Weinberg et al., "Cholecystokinin A and B Receptors Are Differentially Expressed in Normal Pancreas and Pancreatic Adenocarcinoma," The Journal of Clinical Investigation. vol. 100, No. 3 pp. 597-603 (1997).

Weiner, L.M., "An Overview of Monoclonal Antibody Therapy Cancer," Seminars in Oncology. vol. 26, No. 4, Suppl. 12 pp. 41-50 (1999).

Weinstock et al., "Binding of Gastrin$_{17}$ to Human Gastric Carcinoma Cell Lines," Cancer Research. vol. 48, No. 4 pp. 932-937 (1988).

Wendlberger et al, "The syntheses of human big gastrin I and its 32-leucine analog," Chemical Abstracts. vol. 92, No. 21 p. 722 (1980) [Abstract # 92:198749s].

Wetscher et al., "Pathophysiology of Gastroesophageal Reflux Disease," R.A. Heinder ed., R.G. Landes Co., Chapter 2 pp. 7-29 (1993).

Wong et al., "Postprandial hypergastrinaemia in patients with colorectal cancer," Gut. vol. 32 pp. 1352-1354 (1991).

Wunsch, E., and Moroder, L., "Biological and Immunological Properties of Human Gastrin I Analogues," Hoppe-Syeler's Z. Physiol. Chem. vol. 363 pp. 665-669 (1982).

Yamaguchi et al., "Amino-terminal immunoreactivity of big gastrin in plasma and tumors obtained from patients with Zollinger-Ellison Syndrome," Chem. Abstracts vol. 100 p. 373 (1984) [Abstract # 100:154661m].

Yanaihara et al. "A New Type of Gastrin Derivative and its Use for Production of Central Region-Specific Anti-Gastrin Sera," Biomedical Research. vol. 1 pp. 242-247 (1980).

Yanaihara et al. "Human Big Gastrin *N*-Terminal Fragment Immunoreactivity," Gut Peptides, Elsevier, North-Holland Biomed. Press, pp. 26-33 (1979).

Yuki et al., "YM022, A Potent and Selective Gastrin/CCK-B Receptor Antagonist, Inhibits Peptone Meal-Induced Gastric Acid Secretion in Heidenhain Pouch Dogs," Digestive Diseases and Sciences. vol. 42, No. 4 pp. 707-714 (1997).

Zeitoun, "Comparison of Omeprazole with Ranitidine in the Treatment of Reflux Oesophagitis," Scand. J. Gastroenterol. vol. 24, Suppl. 166 pp. 83-87 (1989).

Zeng et al., "Localization of PACAP Receptors on Rat Fundic ECL and D Cells," Gastroenterology. vol. 110, Suppl. 4 p. A1136 (1996) [Abstract].

Zhou et al., "Pre- and Postoperative Sequential Study on the Serum Gastrin Level in Patients with Lung Cancer," Journal of Surgical Oncology. vol. 51 pp. 22-25 (1992).

* cited by examiner

SEQUENCE LISTING

<160> NUMBER OF SEQ ID NOS: 21

<210> SEQ ID NO 1
<211> LENGTH: 101
<212> TYPE: PRT
<213> ORGANISM: Homo sapiens

<400> SEQUENCE: 1

Met Gln Arg Leu Cys Val Tyr Val Leu Ile Phe Ala Leu Ala Leu Ala
1               5                   10                  15

Ala Phe Ser Glu Ala Ser Trp Lys Pro Arg Ser Gln Gln Pro Asp Ala
            20                  25                  30

Pro Leu Gly Thr Gly Ala Asn Arg Asp Leu Glu Leu Pro Trp Leu Glu
        35                  40                  45

Gln Gln Gly Pro Ala Ser His His Arg Arg Gln Leu Gly Pro Gln Gly
    50                  55                  60

Pro Pro His Leu Val Ala Asp Pro Ser Lys Lys Gln Gly Pro Trp Leu
65                  70                  75                  80

Glu Glu Glu Glu Glu Ala Tyr Gly Trp Met Asp Phe Gly Arg Arg Ser
                85                  90                  95

Ala Glu Asp Glu Asn
            100

<210> SEQ ID NO 2
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (17)..(17)
<223> OTHER INFORMATION: AMIDATION

<400> SEQUENCE: 2

Glu Gly Pro Trp Leu Glu Glu Glu Glu Ala Tyr Gly Trp Met Asp
1               5                   10                  15

Phe

<210> SEQ ID NO 3
<211> LENGTH: 18
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 3

Glu Gly Pro Trp Leu Glu Glu Glu Glu Ala Tyr Gly Trp Met Asp
1               5                   10                  15

Phe Gly

<210> SEQ ID NO 4
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

```
<220> FEATURE:
<221> NAME/KEY: MOD_RES
<222> LOCATION: (34)..(34)
<223> OTHER INFORMATION: AMIDATION

<400> SEQUENCE: 4

Glu Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
            20                  25                  30

Asp Phe

<210> SEQ ID NO 5
<211> LENGTH: 35
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 5

Glu Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
            20                  25                  30

Asp Phe Gly
        35

<210> SEQ ID NO 6
<211> LENGTH: 9
<212> TYPE: PRT
<213> ORGANISM: Homo sapiens

<400> SEQUENCE: 6

Ser Trp Lys Pro Arg Ser Gln Gln Pro
1               5

<210> SEQ ID NO 7
<211> LENGTH: 9
<212> TYPE: PRT
<213> ORGANISM: Homo sapiens

<400> SEQUENCE: 7

Ser Gln Gln Pro Asp Ala Pro Leu Gly
1               5

<210> SEQ ID NO 8
<211> LENGTH: 9
<212> TYPE: PRT
<213> ORGANISM: Homo sapiens

<400> SEQUENCE: 8

Gly Arg Arg Ser Ala Glu Asp Glu Asn
1               5

<210> SEQ ID NO 9
<211> LENGTH: 6
<212> TYPE: PRT
<213> ORGANISM: Artificial Sequence
<220> FEATURE:
<223> OTHER INFORMATION: synthetic

<400> SEQUENCE: 9

Pro Pro Gly Gly Pro Pro
```

```
1               5

<210> SEQ ID NO 10
<211> LENGTH: 18
<212> TYPE: PRT
<213> ORGANISM: Homo sapiens

<400> SEQUENCE: 10

Ser Trp Lys Pro Arg Ser Gln Gln Pro Gly Arg Arg Ser Ala Glu Asp
1               5                   10                  15

Glu Asn

<210> SEQ ID NO 11
<211> LENGTH: 18
<212> TYPE: PRT
<213> ORGANISM: Homo sapiens

<400> SEQUENCE: 11

Ser Gln Gln Pro Asp Ala Pro Leu Gly Gly Arg Arg Ser Ala Glu Asp
1               5                   10                  15

Glu Asn

<210> SEQ ID NO 12
<211> LENGTH: 20
<212> TYPE: PRT
<213> ORGANISM: Homo sapiens

<400> SEQUENCE: 12

Ser Trp Lys Pro Arg Ser Gln Gln Pro Gly Gly Gly Arg Arg Ser Ala
1               5                   10                  15

Glu Asp Glu Asn
            20

<210> SEQ ID NO 13
<211> LENGTH: 19
<212> TYPE: PRT
<213> ORGANISM: Homo sapiens

<400> SEQUENCE: 13

Ser Trp Lys Pro Arg Ser Gln Gln Pro Pro Gly Arg Arg Ser Ala Glu
1               5                   10                  15

Asp Glu Asn

<210> SEQ ID NO 14
<211> LENGTH: 23
<212> TYPE: PRT
<213> ORGANISM: Homo sapiens

<400> SEQUENCE: 14

Ser Trp Lys Pro Arg Ser Gln Gln Pro Pro Gly Gly Pro Pro Gly Arg
1               5                   10                  15

Arg Ser Ala Glu Asp Glu Asn
            20

<210> SEQ ID NO 15
<211> LENGTH: 24
<212> TYPE: PRT
<213> ORGANISM: Homo sapiens

<400> SEQUENCE: 15

Ser Gln Gln Pro Asp Ala Pro Leu Gly Pro Pro Gly Gly Pro Pro Gly
1               5                   10                  15
```

Arg Arg Ser Ala Glu Asp Glu Asn
            20

<210> SEQ ID NO 16
<211> LENGTH: 11
<212> TYPE: PRT
<213> ORGANISM: Homo sapiens

<400> SEQUENCE: 16

Ser Trp Lys Pro Arg Ser Gln Gln Pro Pro Cys
1               5                   10

<210> SEQ ID NO 17
<211> LENGTH: 9
<212> TYPE: PRT
<213> ORGANISM: Homo sapiens

<400> SEQUENCE: 17

Ser Trp Lys Pro Arg Ser Gln Gln Pro
1               5

<210> SEQ ID NO 18
<211> LENGTH: 12
<212> TYPE: PRT
<213> ORGANISM: Homo sapiens

<400> SEQUENCE: 18

Ser Gln Gln Pro Asp Ala Pro Leu Gly Pro Pro Cys
1               5                   10

<210> SEQ ID NO 19
<211> LENGTH: 9
<212> TYPE: PRT
<213> ORGANISM: Homo sapiens

<400> SEQUENCE: 19

Ser Gln Gln Pro Asp Ala Pro Leu Gly
1               5

<210> SEQ ID NO 20
<211> LENGTH: 12
<212> TYPE: PRT
<213> ORGANISM: Homo sapiens

<400> SEQUENCE: 20

Cys Pro Pro Gly Arg Arg Ser Ala Glu Asp Glu Asn
1               5                   10

<210> SEQ ID NO 21
<211> LENGTH: 9
<212> TYPE: PRT
<213> ORGANISM: Homo sapiens

<400> SEQUENCE: 21

Gly Arg Arg Ser Ala Glu Asp Glu Asn
1               5

MONOCLONAL ANTIBODIES TO PROGASTRIN

This application is the national stage of PCT International Application No. PCT/IB2005/002793, filed Sep. 21, 2005, entitled "Monoclonal Antibodies To Progastrin," which claims priority to U.S. provisional Application Ser. No. 60/612,224, filed Sep. 22, 2004, entitled "Monoclonal Antibodies To Progastrin." Each of the above noted applications is incorporated by reference herein.

FIELD OF THE INVENTION

The invention relates to antibodies directed against specific regions of the gastrin hormone precursor, progastrin, found in vivo in an animal, particularly a human. The invention further relates to the application of these monoclonal antibodies (MAbs) to detection, diagnosis and monitoring of gastrin-promoted diseases and conditions, and to methods of use of the MAbs of the invention for the prevention and treatment of gastrin-promoted diseases and conditions. The invention also relates to surrogate molecules and their use as reference standards in immunoasssays, particularly as applied to peptide hormones.

BACKGROUND OF THE INVENTION

Human preprogastrin, a peptide of 101 amino acids, is the primary translation product of the gastrin gene and has the following structure:

```
                                       (SEQ ID NO: 1)
MQRLCVYVLI FALALAAFSE ASWKPRSQQP DAPLGTGANR

DLELPWLEQQ GPASHHRRQL GPQGPPHLVA DPSKKQGPWL

EEEEEAYGWM DFGRRSAEDE N.
```

Progastrin is formed by cleavage of the first 21 amino acids (constituting the signal peptide) from preprogastrin. The 80 amino acid long chain of progastrin is further processed by cleavage and modifying enzymes to several biologically active gastrin hormone forms, including gastrin-17 (G17), gastrin-34 (G34), glycine extended gastrin-17 (G17-Gly),and glycine extended gastrin-34 (G34-Gly).

Mature G17 is modifed at both amino- and carboxy-terminal residues: the N-terminal glutamine is cyclized to form pyroglutamic acid (pGlu) and the free carboxyl group of the C-terminal phenylalanine residue is amidated by the enzyme, peptidyl α-amidating mono-oxygenase (PAM) to form a C-terminal Phe-$NH_2$. Mature G34 is identically amidated at its C-terminal end to form a C-terminal Phe-$NH_2$. (See Dockray et al., Ann. Rev. Physiol. (2001) 63: 119-139).

Mature G17, the predominant form of "little" gastrin in humans, has the amino acid sequence: pEGPWLEEEEE-AYGWMDF-$NH_2$ (SEQ ID NO: 2). G17-Gly is an incompletely processed form of gastrin found as a minor component of "little" gastrin in healthy human subjects and has the amino acid sequence: pEGPWLEEEEEAYGWMDFG (SEQ ID NO: 3).

Gastrin-34, the predominant form of "big" gastrin in humans, has the amino acid sequence: pELGPQGPPHL-VADPSKKQGPWLEEEEEAYGWMDF-$NH_2$ (SEQ ID NO: 4). Glycine-extended gastrin 34 (G34-Gly) has a C-terminal glycine residue, and has the amino acid sequence:

```
                                       (SEQ ID NO: 5)
pELGPQGPPHLVADPSKKQGPWLEEEEEAYGWMDFG.
```

Gastrin is secreted by the pyloric antral-G cells of the stomach in response to gastrin-releasing peptide (GRP), and is suppressed by gastric acid and the paracrine action of several peptide hormones, most notably, somatostatin. It has long been recognized that gastrin peptides function to stimulate acid secretion in the stomach of healthy individuals, however, it has only recently been shown that these peptides also control proliferation, differentiation and maturation of different cell types in the gastrointestinal (GI) system.

Progastrin is normally fully processed to gastrin hormone forms. When produced in excess, progastrin is at least partly processed to one or more forms of gastrin hormone that act on the gastrointestinal system and may potentiate the formation of gastrin-promoted tumors. In some cases the progastrin is circulated in the blood and can be detected in the urine of patients suffering from progastrin-promoted diseases or conditions.

In addition to their local activity in the GI system, G17 and, to a lesser extent, G17-Gly are released into the bloodstream and have been found to increase in the serum of patients afflicted with gastrointestinal disorders and diseases, such as gastric cancer, colorectal cancer, and pancreatic cancer. These gastrin species have more recently also been found to be associated with other diseases not associated with the gastrointestinal tract, including small cell lung cancer (SCLC) and liver metastasized tumors. See for example "Gastrin and Colon Cancer: a unifying hypothesis" S. N. Joshi et al., *Digestive Diseases* (1996) 14: 334-344; and "Gastrin and Colorectal Cancer" Smith, A. M. and Watson, S. A. (2000) *Alimentary Pharmacology and Therapeutics* 14(10): 1231-1247.

Antibodies are key reagents in numerous assay techniques used in medical, veterinary and other immunodetection fields. Such tests include many routinely used immunoassay techniques, such as for example, enzyme-linked immunosorbant assays (ELISA), radioimmunoassays (RIA), immunohistochemistry (IHC), and immunofluorescence (IF) assays.

Anti-gastrin polyclonal antibodies have been shown to be effective in inhibiting gastrin activity ("Inhibition of gastrin activity by incubation with antibodies to the C-terminal tetrapeptide of gastrin" Jaffe et al., *Surgery* (1969) 65(4):633-639); and non-human anti-gastrin polyclonal antibodies have been applied to therapy in a patient suffering from Zollinger-Ellison syndrome, a pathological condition in which excessive gastrin is produced without stimulation by feeding. See Hughes et al., "Therapy with Gastrin Antibody in the Zollinger-Ellison Syndrome" Hughes et al., *Digestive Diseases* (1976) 21(3):201-204. However, these rabbit anti-gastrin antibodies had "at best a short term effect in this patient." (Hughes at p. 204). U.S. Pat. Nos. 5,886,128 and 5,785,970 disclose methods of treatment of ulcers or tumors whose growth is dependent on or stimulated by gastrin hormones by immunizing with gastrin hormone peptide conjugates.

Until now, MAbs capable of sensitively detecting, and accurately distinguishing progastrin from the processed forms of gastrin hormone have not been available. Furthermore, until the present invention, it was not possible to accurately measure the amount progastrin in a sample, such as for instance a sample of biological fluid. The MAbs of the invention can be used in assays for clinical testing to precisely define the biology of progastrin in normal and disease states. The invention also provides MAb compositions for pharmaceutical use and methods for the prevention and treatment of progastrin-promoted diseases and conditions.

SUMMARY OF THE INVENTION

The present invention provides a progastrin-binding molecule that selectively binds progastrin, wherein the molecule does not bind gastrin-17(G17), gastrin-34(G34), glycine-extended gastrin-17(G17-Gly), or glycine-extended gastrin-34 (G34-Gly). The progastrin-binding molecule may be an antibody molecule, such as a monoclonal antibody, an antibody binding region, or a single chain antibody.

In one aspect, the invention provides a monoclonal antibody (MAbs) that selectively binds progastrin at an epitope within the amino acid sequence 1-9 of progastrin, i.e. SWKPRSQQP (SEQ ID NO: 6). Hybridomas that produce the MAbs that selectively bind progastrin at an epitope within the amino acid sequence 1-9 of progastrin, i.e. SWKPRSQQP (SEQ ID NO: 6) are also provided.

In another aspect, the present invention provides a MAb that selectively binds progastrin at an epitope within the amino acid sequence 6-14, i.e. SQQPDAPLG (SEQ ID NO: 7). Hybridomas that produce MAbs that selectively bind progastrin at an epitope within the amino acid sequence 6-14, SQQPDAPLG (SEQ ID NO: 7) are also provided.

In yet another aspect, the present invention provides a MAb that selectively binds progastrin at an epitope within the amino acid sequence 72-80 of progastrin, GRRSAEDEN (SEQ ID NO: 8). Hybridomas that produce MAbs that selectively bind progastrin at an epitope within the amino acid sequence 72-80, GRRSAEDEN (SEQ ID NO: 8) are also provided.

According to the present invention, combinations of two or more of the a progastrin, wherein the molecule does not bind gastrin-17(G17), gastrin-34(G34), glycine-extended gastrin-17(G17-Gly), or glycine-extended gastrin-34(G34-Gly) can be used in a panel of progastrin-binding molecules.

Also provided are pharmaceutical compositions of a progastrin-binding molecule, wherein the molecule does not bind gastrin-17(G17), gastrin-34(G34), glycine-extended gastrin-17(G17-Gly), or glycine-extended gastrin-34(G34-Gly) in combination with a pharmaceutically acceptable carrier. In a particular aspect, the invention provides pharmaceutical compositions of a MAb that selectively binds: (1) progastrin at an epitope within the amino acid sequence corresponding to amino acids 1-9 of progastrin, SWKPRSQQP (SEQ ID NO: 6); (2) progastrin at an epitope within the amino acid sequence 6-14, SQQPDAPLG (SEQ ID NO: 7); or (3) progastrin at an epitope within the amino acid sequence of 72-80, GRRSAEDEN (SEQ ID NO: 8); in combination with a pharmaceutically acceptable carrier.

The present invention still further provides a progastrin immunoassay. The method includes: first, obtaining a sample to be assayed for progastrin and contacting the sample with a progastrin-binding molecule that does not bind gastrin-17 (G17), gastrin-34(G34), glycine-extended gastrin-17(G17-Gly), or glycine-extended gastrin-34(G34-Gly), under suitable conditions for binding and allowing any progastrin present to form a progastrin-progastrin-binding molecule complex; then detecting the presence or absence of the progastrin-progastrin-binding molecule complex; and/or determining the amount of progastrin-progastrin-binding molecule complex in the sample by an immunoassay method.

The present invention further provides methods of diagnosing a gastrin-promoted disease or condition in a patient by determining the level of progastrin in a sample of a biological fluid from the patient and comparing the level of progastrin in the sample with the level of progastrin in a sample of biological fluid from one or more control individuals or with a reference standard. Such gastrin-promoted diseases or conditions can be prevented or treated by administering to a patient in need thereof a pharmaceutical composition including a progastrin-binding molecule that selectively binds: (1) progastrin at an epitope within the amino acid sequence corresponding to amino acids 1-9 of progastrin, SWKPRSQQP (SEQ ID NO: 6); (2) progastrin at an epitope within the amino acid sequence 6-14 of progastrin, SQQPDAPLG (SEQ ID NO: 7); or (3) progastrin at an epitope within the amino acid sequence 72-80 of progastrin, GRRSAEDEN (SEQ ID NO: 8).

A method of monitoring a gastrin-promoted disease or condition in a patient is also provided. The method includes determining the level of progastrin in a sample of a biological fluid from a patient suffering from or at risk of a gastrin-promoted disease or condition at a first time point; determining the level of progastrin in one or more samples of the biological fluid from the patient at one or more different time points; comparing the levels of progastrin determined at different time points and thereby monitoring the gastrin-promoted disease or condition.

The invention further provides a kit for performing an immunoassay, including an anti-progastrin-binding molecule and a suitable container. The progastrin-binding molecule selectively binds progastrin, but does not bind gastrin-17 (G17), gastrin-34(G34), glycine-extended gastrin-17(G17-Gly), or glycine-extended gastrin-34(G34-Gly).

Also provided is a surrogate reference standard (SRS) molecule that consists essentially of a peptide chain of from about 10 to about 35 amino acids. The SRS molecule includes immunomimics of at least two epitopes found in a protein of interest of greater than about 50 amino acids.

The invention also further provides a method of standardizing a sandwich immunoassay for an protein of interest of greater than about 50 amino acids comprising a first and a second epitope, the method comprising detecting or measuring a signal generated in the immunoassay with a standard amount of a surrogate reference standard (SRS) molecule. The SRS molecule consists essentially of a peptide chain of between from 10 to about 35 amino acids that includes immunomimics of the first and second epitopes of the protein of interest.

DETAILED DESCRIPTION OF THE INVENTION

The following provides the definitions of terms and phrases as used in this specification:

As used herein, "preprogastrin" is the 101 amino acid primary translation product of the gastrin gene and includes the N-terminal 21 amino acid signal sequence, the pro-peptide sequences and the gastrin hormone sequences.

As used herein, "Progastrin" is the 80 amino acid product formed after cleavage of the twenty-one amino acid signal sequence from preprogastrin. "Progastrin" is the primary precursor of all biologically active forms of gastrin hormone.

As used herein a "progastrin-immunomimic" is a moiety that elicits antibodies that bind progastrin and are bound by anti-progastrin antibodies. As used herein, the progastrin immunomimic moieties do not bind gastrin-17 (G17), whether amidated at the C-terminus or having a free C-terminus; glycine extended gastrin-17 (G17-Gly); gastrin-34

(G34) including both the C-terminally amidated form and the form having a free C-terminus; or glycine extended gastrin-34 (G34-Gly).

As used herein, a "gastrin hormone" or a "gastrin hormone form" are used interchangeably and mean any biologically active and/or immunologically cross-reactive gastrin hormone peptide. The major forms of gastrin hormone include, but are not limited to gastrin-17 (G17), whether amidated at the C-terminus or having a free C-terminus; glycine extended gastrin-17 (G17-Gly); gastrin-34, (G34) including both the C-terminally amidated form and the form having a free C-terminus; glycine extended gastrin-34 (G34-Gly).

A "biological fluid" as used herein means any fluid that includes material of biological origin. Preferred biological fluids for use in the present invention include bodily fluids of an animal, e.g. a mammal, preferably a human subject. The bodily fluid may be any bodily fluid, including but not limited to blood, plasma, serum, lymph, cerebrospinal fluid (CSF), saliva, sweat and urine.

A "preservative agent" as used herein means any agent, supplement or additive that reduces the time dependent degradation of gastrin in a sample of biological fluid, or a liquid sample comprising a biological component. Preservative agents useful in the practice of the present invention include any of the many preservative agents well known in the art, including but not limited to general chemical preservatives, such as for instance, sodium azide, EDTA and protease inhibitors, such as for instance, PMSF (Phenylmethylsulfonylfluoride), and aprotinin (e.g. Trasylol), or a biological preservative, such as for instance, heparin.

A "progastrin-binding molecule" as used herein may be any molecule that binds progastrin, but does not bind gastrin-17(G17), gastrin-34(G34), glycine-extended gastrin-17 (G17-Gly), or glycine-extended gastrin-34(G34-Gly).

A "gastrin-promoted disease or condition" as used herein means any disease or condition in which gastrin and/or progastrin has stimulatory a role. For instance, it is well known that gastrin stimulates growth and proliferation of many forms of tumors, particularly gastro-intestinal tumors, such as colorectal tumors. See U.S. Pat. No. 6,548,066 to Michaeli et al.

The progastrin-binding molecule of the present invention may be any progastrin-binding molecule, such as, for instance, an antibody molecule or a receptor molecule. The antibody molecule may be any antibody molecule, such as a monoclonal antibody. The anti-progastrin antibody molecules may be single chain antibody molecules, or antibody fragments, e.g. Fab fragments, or any other antibody fragment that includes a progastrin-binding region. Preferably, the anti-progastrin antibody molecules of the invention are mammalian antibody molecules, such as rabbit, mouse or human antibody molecules. The anti-progastrin antibody molecules of the invention may be chimeric human/non-human antibodies (e.g. human/mouse chimeras), humanized or fully human antibodies.

Monoclonal antibodies (MAbs) have unique characteristics that render them superior in many respects to polyclonal antisera and to antibodies purified from polyclonal antisera when used in many of these assays. These attributes include monodeterminant specificity for the target antigen (i.e. specificity for a single epitope), unchanging specificity among different antibody preparations, as well as unchanging affinity and chemical composition over time. Furthermore, MAbs can be produced indefinitely and in unlimited amounts by in vitro methods. These properties are in sharp contrast to those of polyclonal antibodies, which require in vivo immunization methods with the unavoidable associated biological variability and limited antibody production capacity over the lifespan of the immunized animal.

Despite these advantages, differences exist between individual MAbs even though they may be specific for the same epitope. For example, differences between MAbs induced by immunization with a single antigenic epitope region can arise with respect to any or all of the following characteristics: 1) the fine specificity for the molecular composition and tertiary structure of the epitope; 2) the antibody idiotype; 3) the antibody affinity; 4) the antibody allotype; and 5) the antibody isotype. These characteristic differences can affect the behavior of MAbs in a particular immunoassay, such that different MAb isolates raised against the same antigenic region can behave differently in a given assay. Consequently, some MAbs will be superior to others that bind the same epitope when used as reagents in a particular immunoassay.

The anti-progastrin binding molecules of the present invention, especially the anti-progastrin MAbs, are particularly useful in an immunoassay. The immunoassay may be an enzyme-linked immunosorbent assay (ELISA), a radioimmunoassay (RIA), an immunodiffusion assay, or an immunodetection assay, such as a surface plasmon resistance assay (e.g. a Biacore® assay), an ELISPOT, slot-blot, or a western blot. As a general guide to such techniques, see for instance, Ausubel et al. (eds) (1987) in "*Current Protocols in Molecular Biology*" John Wiley and Sons, New York, N.Y.

In a particularly useful embodiment the progastrin-binding molecules of the present invention can be used in an immunoassay such as an immunohistochemical (IHC) staining assay or an immunofluorescence (IF) procedure for visualization of a form of gastrin hormone in a tissue sample. See for example "*Principles and Practice of Immunoassay*" (1991) Christopher P. Price and David J. Neoman (eds), Stockton Press, New York, N.Y.

Immunohistochemical staining is of great value in detection and diagnosis of tumors, see for instance, Bodey, B. "The significance of immunohistochemistry in the diagnosis and therapy of neoplasms" (2002) *Expert Opin Biol Ther.* 2(4): 371-93. See also Osin P P, Lakhani S R. (1999) The Pathology of Familial Breast Cancer: Immunohistochemistry and Molecular Analysis. *Breast Cancer Res.* 1(1):36-40.

Anti-Progastrin Monoclonal Antibodies

Selection of the optimal monoclonal antibody (MAb) for use in a particular application is preferably achieved by assessing the performance of each of the individual candidate MAbs in the particular intended application. For this reason, testing of candidate MAbs for optimum functionality in the intended application is part of the selective process to derive a MAb that is optimal for the intended use. This selective step is performed in addition to the selection steps normally undertaken in deriving MAbs, which include binding to the targeted antigen and serial cloning of the hybridoma that produces the MAb to ensure stability of the essential characteristics of the hybridoma cell line, including persistent cell growth and division, and consistent unlimited antibody production over an indefinite period.

As used herein, an antibody that is "selective" for a particular target epitope of progastrin means that the antibody binds the particular target epitope of progastrin with a $K_a$ of at least about ten times higher than any other gastrin epitope, preferably one hundred times higher than any other gastrin epitope, and most preferably at least about one thousand times higher than any other gastrin epitope.

In one aspect, the present invention provides a method of identifying MAbs selective for the N-terminal and C-terminal of progastrin, wherein the MAbs have superior properties.

These MAbs are particularly suitable for use in an immunoenzymometric assay (commonly termed an "ELISA" or enzyme-linked immunosorbent assay) designed to measure the particular form of gastrin hormone in a fluid, especially in a biological fluid.

The MAbs of the present invention are also suitable for detecting and/or quantifying gastrin hormone in immunodetection assays, such as for instance ELISPOT, radioimmunoassay, antibody-based sandwich capture assays, surface plasmon resistance detector systems (such as Biacore®-type systems), dot-blot, slot blot and western blot assays, as well as immunofluorescence and immunohistochemical assays.

In another aspect, the present invention provides MAbs that selectively bind progastrin at an epitope within the amino acid sequence 1-9 of progastrin (SWKPRSQQP, SEQ ID NO: 6), i.e. the product formed after cleavage of the twenty-one amino acid signal sequence form preprogastrin (the primary translation product of the gastrin gene).

In still another aspect, the present invention provides MAbs that selectively bind progastrin at an epitope within the amino acid sequence 6-14 of progastrin (SQQPDAPLG, SEQ ID NO: 7), i.e. the product formed after cleavage of the twenty-one amino acid signal sequence form preprogastrin (the primary translation product of the gastrin gene) followed by the additional removal of amino acids 1-5 of progastrin.

In a further aspect, the present invention provides MAbs that selectively bind progastrin at an epitope within the amino acid sequence 72-80 of the C-terminal region of progastrin (GRRSAEDEN, SEQ ID NO: 8) i.e. the product formed after cleavage of the twenty-one amino acid signal sequence form preprogastrin (the primary translation product of the gastrin gene).

In yet a further aspect, the invention provides MAbs that selectively bind progastrin. These Mabs bind progastrin, but do not bind the processed gastrin hormone forms: G17, G34, G17-Gly or G34-Gly. The MAbs of the invention selective for progastrin include MAbs that bind the C-terminal region of human progastrin. These MAbs that bind the C-terminal region of human progastrin also bind preprogastrin, which consists of a peptide chain of 101 amino acids from which progastrin, and gastrin are sequentially processed. However, processing of preprogastrin is rapid and occurs at the endoplasmic reticulum (ER) where it is synthesized. The MAbs of the invention that bind progastrin are useful in assays described herein to detect and quantitate progastrin in a sample.

The MAbs of the present invention can be chimerized or humanized according to established techniques well known in the art. See for instance, U.S. Pat. No. 4,816,567 to Cabilly entitled "Recombinant immunoglobin preparations" and U.S. Pat. No. 6,689,869 entitled "Labeled humanized anti-CD-18 antibodies and fragments and kits" to Waldman et al., and U.S. Pat. No. 6,639,055 entitled "Method for making humanized antibodies" to Carter et al. The humanized antibody can be reshaped to more closely match the binding affinity of the original mouse Mab. See for instance, U.S. Pat. No. 6,699,974 entitled "Re-shaped human anti-HM1.24 antibody" to Ono et al.

The present invention also provides methods for detection of progastrin samples, especially of biological samples such as biological fluids and cells, tissues, biopsy samples and organ sections etc. The invention further provides methods of diagnosis of a gastrin-promoted disease or condition in a patient by determining the presence of progastrin in diseased or in normal tissue and cells. The methods include determining the level of progastrin in a sample of a biological fluid from the patient and comparing the level of progastrin in the patient sample with the level of progastrin in a sample of biological fluid from one or more control individuals. The sample from the control individuals can be a pooled biological fluid from healthy individuals. Alternatively, the level of progastrin in the patient sample can be compared with a reference standard. The reference standard can be a standard calibrated to be within the normal range for progastrin in healthy individuals. Such control samples can readily be prepared by those of skill in the art without undue experimentation. See also below for Surrogate Reference Standards.

These methods of detection and diagnosis can be achieved by means of immunohistochemical staining of biopsy specimens using an anti-progastrin MAb of the invention. Binding of anti-progastrin Mabs to tissue samples can be visualized by immunohistochemical methods, such as, for instance, by fluorescence, immunogold or enzyme-promoted staining. For a general review of immunohistochemistry in diagnostic procedures see for example, Miller et al., Fixation and epitope retrieval in diagnostic immunohistochemistry: a concise review with practical considerations. *Appl. Immunohistochem. Mol. Morphol.* (2000) 8(3): 228-235.

By such methods, one skilled in the art can utilize the anti-progastrin Mabs of the present invention to assess tissues, including diseased, cancerous or pre-cancerous tissue, for the presence and distribution of progastrin. This information can be useful for diagnosis and can also be helpful for selection of appropriate treatments for the diagnosed gastrin-promoted or progastrin-promoted diseases and conditions.

Surrogate Reference Standards

Antibody-based assays for an antigen in which the antigen is detected or measured in an assay system that relies on binding of antibodies directed against two separate epitopes expressed by the antigen, can be limited in practical utility under certain circumstances. Such is the case when the reference antigen for the assay, against which antigen in test samples is quantified, cannot be readily obtained or synthesized. For example, in the progastrin sandwich ELISA described in the present application, a standard curve is generated using serial dilutions of a solution of reference antigen at a known concentration.

Thus, the assay to quantitate progastrin can be run to establish a standard curve using a dilution series of progastrin. This standard curve of progastrin concentration against signal produced enables quantitation of progastrin in test samples by comparison of the signal obtained with the test sample and reading the concentration of progastrin from the standard curve. The limitation of this procedure is that some antigens may be difficult, or excessively costly, to obtain in pure form and in sufficient quantity to produce a practical assay for clinical use. For example, purified progastrin (a prohormone of 80 amino acids), is costly to produce and difficult to accurately synthesize. These restrictions would severely limit the practicality of the capture ELISA for progastrin, which relies on antibodies binding to the two terminal ends of the molecule.

A solution to this problem is to substitute a Surrogate Reference Standard (SRS) in place of the native molecule. The SRS contains both of the epitopes expressed by the native molecule that are required for the immunoassay, enabling both capture and detection antibodies to bind the SRS. However, the intervening region (and/or the regions from each epitope to the end) of the native molecule is eliminated, replaced or shortened in the SRS, such that the SRS is significantly shorter than the native molecule and thus can be readily synthesized at a reasonable cost.

Peptides of up to about 35 amino acids in length can be readily and economically synthesized by existing peptide synthesis methods. Thus, the addition of a linker of from one to up to about twenty amino acids linking the two epitopes of the SRS is practical. In particular embodiments, the linker can be from about four to about fifteen amino acids in length, or from about eight to about twelve amino acids in length. Linkers can be designed to enhance assay performance by selection a linker of appropriate length and character (such as rigidity or flexibility, hydrophilicity or hydrophobicity, and the like) for optimum performance in the particular immunoassay in which the SRS is to serve as a reference standard.

The concept of the surrogate reference standard is broadly applicable to assays wherein a simpler synthetic compound can serve as a surrogate for a more complicated natural compound. Thus, in the case of sandwich ELISAs wherein antigen is captured by antibody of one specificity and detected by antibody of a second specificity, the SRS has the general structure:

[X-epitope 1-L-epitope 2-Y]

where epitope 1 and epitope 2 are immunomimics of different epitopes of the native molecule, such that antibodies that bind epitope 1 or epitope 2 also bind the corresponding epitope of the native molecule. The SRS molecule is between about 10 and about 35 amino acids in length. Epitope 1 and epitope 2 are joined by a linker, L which may be a peptide or a non-peptide linker, or L may be a covalent bond. X and Y can each be an amino acid, a peptide sequence or a blocking group. Alternatively, either X or Y, or both can be a hydrogen atom of the N-terminus or the C-terminus, respectively, of the SRS.

Linkers useful in the practice of the present invention include any linker moiety. Such moieties are well known in the art. For instance, useful peptide linker moieties include gly-gly, as described in U.S. Pat. No. 5,759,551, issued to Ladd et al., col. 9, line 64; the inactive peptides of U.S. Pat. No. 6,613,530, issued to Wienhues et al., col. 3, lines 38-47; and the proline rich flexible hinge spacers disclosed in U.S. Pat. No. 5,683,695, issued to Shen et al. Further, non-peptide spacer moieties are also useful and have the added feature that they are generally protease resistant. Such moieties include, for instance, —O—R—CO—, —NH—R—CO—, —NH—R—NH—, —O—R—NH—, or —, —NH—R—CH$_2$—, in which R is a saturated or unsaturated hydrocarbon chain optionally substituted and/or interrupted by one or more aromatic radicals or heteroatoms, e.g. a nitrogen atom, an oxygen atom or a sulfur atom, as disclosed in U.S. Pat. Nos. 5,736,146, and 5,869,058, both issued to Cohen et al. The non-peptide chemical linkers disclosed in U.S. Pat. No. 6,780,969 to Wang are also useful in the practice of the present invention.

Progastrin is a large peptide of 80 amino acids that is difficult and expensive to purify in quantity. An SRS consisting of the progastrin N terminal epitope (e.g. progastrin amino acids 1-9), optionally followed by a short linker, attached to a progastrin C terminal epitope (e.g. amino acids 72-80) can be synthesized by routine methods, such as by solid phase peptide synthesis. The linker may be any linker, such as for instance an amino acid, a peptide or a non-peptide linker. The SRS is useful for standardizing a progastrin immunoassay.

In a particular embodiment, the Progastrin SRS includes two epitope-containing peptides of 9 amino acids each, optionally connected by a linker sequence between the two peptides. Shorter or longer length epitope-containing peptide sequences can be substituted, provided that the total length of the SRS does not exceed about 35 amino acid residues in length and that sufficient binding of the antibodies to their respective cognate epitopes is retained for adequate performance of the assay.

If a peptide linker is included between the two progastrin epitopes as described above, the length of the Progastrin SRS peptide is increased by the length of the linker. For example, a linker of -Pro-Pro- or of -Gly-Gly- increases the total peptide length from 18 to 20 amino acids. Longer amino acid linkers can be substituted; the optimal sequence being selected for use as the Progastrin SRS. In a preferred embodiment the linker is a peptide that includes combinations of Proline and Glycine, such as, for instance -Pro-Pro-Gly-Gly-Pro-Pro- (SEQ ID NO: 9). Such peptides of up to about 35 amino acids in length can be readily synthesized in large quantities to a high level of purity at reasonable cost by standard methods. See for example Merrifield, *Methods in Enzymology* (1997), 289: 3-13; Also, Wade & Tragear, Solid Phase Peptide Synthesis, *Australas. Biotechnol.* (1993) 3(6): 332-6.

The Progastrin SRS can be used in place of an authentic progastrin reference standard as follows. A solution of Progastrin SRS would be prepared at the same molar concentration of peptide that would be used if progastrin was the reference standard. A serial dilution of this solution is prepared, then used in the assay to establish the reference curve (Molar concentration vs. signal e.g. absorbance).

Progastrin SRS solutions can be prepared on a molar basis, providing immunometric responses identical to solutions of progastrin itself; similar, or identical standard curves are obtained with a progastrin SRS as with authentic progastrin. Absorbance values obtained from actual test samples, such as human plasma, containing progastrin, can then be compared to the SRS standard curve, to determine the concentrations of progastrin in the test samples. Comparison of the progastrin SRS standard against a progastrin standard need only be performed once and subsequently only to check accuracy.

Alternatively, the SRS can be used to generate an arbitrary standard curve that need never be calibrated against the authentic reference standard molecule. All results are then expressed as arbitrary units based by comparison with a convenient standard concentration of SRS.

The linker element may or may not be required, depending on the attributes of the SRS desired in the particular assay method in which it is to be applied. Examples of progastrin SRS peptides suitable for use in progastrin ELISAs include:

[progastrin 1-9]-[progastrin 72-80]
(SWKPRSQQPGRRSAEDEN, SEQ ID NO: 10).

[progastrin 6-14]-[progastrin 72-80]
(SQQPDAPLGGRRSAEDEN, SEQ ID NO: 11).

[progastrin 1-9]-Gly-Gly-[progastrin 72-80]
(SWKPRSQQPGGGRRSAEDEN, SEQ ID NO: 12).

[progastrin 1-9]-Pro-[progastrin 72-80]
(SWKPRSQQPPGRRSAEDEN, SEQ ID NO: 13).

[progastrin 1-9]-Pro-Gly-Gly-Pro-Pro-[progastrin 72-80]
(SWKPRSQQPPGGPPGRRSAEDEN, SEQ ID NO: 14).

[progastrin 6-14]-Pro-Pro-Gly-Gly-Pro-Pro-[progastrin 72-80]
(SQQPDAPLGPPGGPPGRRSAEDEN, SEQ ID NO: 15).

Additional potential sequences of progastrin SRS peptides can be readily determined without undue experimentation by one skilled in the art. The optimal progastrin SRS peptide for any particular immunoassay can be selected by testing candidate SRS peptides in the immunoassay system and choosing an SRS peptide that mimics authentic progastrin in the concentration range of interest under the conditions (e.g. of temperature and ionic strength, and divalent cation concentration etc.) of the assay.

Panels of Anti-Progastrin Monoclonals

The present invention provides for the first time panels of anti-progastrin and anti-gastrin MAbs that permit unequivocal identification and quantitation of progastrin and gastrin in a sample. Routine immunoassays in which the MAbs of the invention may be used include, but are not limited to, enzyme-linked immunosorbent assays (ELISAs), radioimmunoassays (RIAs), surface plasmon resistance-type assays (e.g. Biacore®-type assays), immunofluorescence assays (IFs), immunohistochemical assays (IHCs), immunodiffusion assays and the like. See for instance, U.S. Pat. No. 5,932,412 entitled "Synthetic peptides in human papilloma virus 1, 5, 6, 8, 11, 16, 18, 31, 33 and 56 useful in immunoassay for diagnostic purposes" to Dillner et al. for examples of routine diagnostic assay methods.

Supplementation of the panel of MAbs with one or more additional MAbs that selectively bind particular gastrin hormone species provides the capability of specific identification and quantitation of more than one gastrin hormone species (produced by processing of progastrin), in addition to the progastrin in a sample. For example, addition of a MAb selective for the N-terminus of the mature G17 form to the above-described panel of antibodies further permits the specific identification and quantitation of mature G17 hormone in a sample in addition to the identification and quantitation of progastrin by the anti-progastrin MAb of the present invention. Similarly, a panel of Mabs including an anti-progastrin MAb of the invention and also a MAb selective for the N-terminus of G34 also allows the specific identification and quantitation of G34 in a sample. Thus, as illustrated above, addition to the panel of a MAb selective for any particular gastrin hormone form can be used to supply further information as to the nature and amounts of the particular gastrin hormone form in the sample in addition to the information related to progastrin obtained with the anti-progastrin MAb of the invention. Other combinations of Mabs useful in a panel of MAbs for identification, quantitation and monitoring of other forms of gastrin hormone will be immediately apparent to those of skill in the art. The present invention encompasses all such pairs of MAbs of the invention and combinations of two or more of MAbs of the invention.

The MAbs of the present invention provide the means to accurately determine the amounts and ratios of progastrin/gastrin hormone forms for assessment of predispositions to gastrin-hormone-promoted diseases and conditions, and for detection and diagnosis of such diseases and conditions in patients suffering therefrom. For example, the anti-gastrin MAbs of the invention can be incorporated into ELISA assays for large scale screening of patient serum or other biological fluid for progastrin and any one or all of the G17, G34, and the G17-Gly, and G34-Gly gastrin hormone forms.

The MAbs of the present invention, combinations of pairs of MAbs selected from the MAbs of the invention, and panels of MAbs of the present invention are particularly useful when applied to high-throughput methods. Such methods include micro-chip and micro-array methods of gastrin hormone antigen detection, such that many samples can be tested on a microplate or slide, or other assay substrate, such as a plate with virtual wells (such as for instance, that described in U.S. Pat. No. 6,565,813 to Garyantes et al). Detection of binding can be by any one of the many state-of-the-art detection systems currently available. Detection of binding can be, for instance, by surface plasmon resistance (SPR) changes caused by specific biomolecular reactions, such as antigen-antibody binding. See also, for example, U.S. Pat. No. 5,981,167 to Taremi et al. for an application of this technology to enzymatic assays. The technology may be applied in a continuous flow mode and is equally applicable to detection of antibody binding to a surface-immobilized peptide or protein, such as a gastrin hormone, or to the detection of a gastrin-antibody complex. The latter complex may be detected by binding to a surface immobilized antibody specific for an epitope of the form of gastrin hormone (G17, G34, G17-Gly or G34-Gly) binding to which is not sterically hindered by the antibody of the complex. Furthermore, this technology has the advantage of high throughput applicability and high sensitivity without the requirement for a radiolabel.

The MAbs of the present invention are also useful for immunohistochemical (IHC) and immunofluorescence (IF) assays of tissue samples, such as for instance, from biopsy material. Such analyses can be used to detect aberrant levels of individual gastrin-hormone forms and hence to diagnose gastrin-hormone-promoted diseases and conditions.

The Mabs of the present invention are also useful for prevention, diagnosis and therapy of progastrin-hormone-promoted diseases and conditions. The anti-progastrin MAbs of the invention can be formulated in pharmaceutical compositions for passive immunization against particular gastrin hormone forms. See for example, U.S. Pat. No. 6,391,299 (herein after the '299 patent) entitled "Anti-factor IX/IXa antibodies" to Blackburn et al. Functional fragments of the MAbs of the present invention, such as, for instance Fab fragments, F(ab')$_2$ fragments and any fragments (see the '299 patent for fragment descriptions) that retain the ability to bind the gastrin hormone form to which they are directed can also be incorporated into pharmaceutical compositions and applied in therapy. See the '299 patent for useful pharmaceutical compositions. The preferred routes of administration of the pharmaceutical compositions of the invention include parenteral routes of administration, such as subcutaneously, intramuscularly and intravenously. Additionally, the oral route can be used for therapy of certain diseases, particularly diseases of the gastrointestinal tract, such as ulcerative diseases of the esophagus or stomach.

Alternatively, the pharmaceutical compositions of the present invention can be delivered intranasally. Such pharmaceutical compositions are particularly useful when administered in an effective amount for the prevention or therapy of gastrin-hormone-promoted diseases or conditions in patients having a prognosis of high likelihood of such diseases or conditions, treatment of patients already suffering from such diseases or conditions. The pharmaceutical compositions of the invention are also useful for the alleviation of symptoms and the arrest of progression of progastrin-promoted diseases and conditions.

An effective amount of a pharmaceutical composition that includes an intact or functional fragment of an anti-gastrin MAb, particularly a humanized anti-gastrin MAb of the invention for the treatment of a gastrin-promoted disease or condition is defined as an amount that prevents onset of or reduces the rate of progression of the disease or condition: more preferably an effective amount is an amount that stabilizes the disease or condition; more preferably still an effective amount is an amount that causes regression of the disease or condition. Most preferably, an effective amount is an amount that completely cures the disease or condition.

Furthermore, the MAbs of the present invention can be applied in immunoassays for monitoring the progression of gastrin-hormone-promoted diseases and conditions, where the level or amount of progastrin provides an indication of the success of treatment or therapy, or of progression of the disease or condition.

Moreover, the MAbs of the present invention are useful in methods of evaluating a progastrin hormone blocking treatment of a patient suffering from a gastrin-hormone-promoted disease or condition. The method includes the steps of:
a) obtaining a first sample of biological fluid from the patient prior to or in the early stages of a treatment;
b) determining the level of progastrin in the first sample by an immunoassay method;
c) obtaining a second sample of biological fluid from the patient after a suitable time within which the treatment would have an effect;
d) determining the level of progastrin in the second sample by the immunoassay method,
e) comparing the determined amounts of progastrin in the first sample with the amount of progastrin in the second sample so as to determine the efficacy of the progastrin binding or blocking treatment.

The above-described method applied to evaluating a progastrin binding treatment or blocking treatment in a patient is particularly valuable in clinical practice, where timing of decisions to proceed with one therapeutic regimen or another may be critical to the outcome for the patient. The method of the present invention provides information on which to base these critical decisions. The method provides a measurement of the progastrin amount prior to or in the early stages of treatment and provides one or more measurements of progastrin at one or more periods after initiation of treatment, particularly when the treatment is expected to have begun to be effective.

The progastrin blocking treatment may be passive administration of anti-progastrin antibody to a patient. The progastrin blocking substance may any progastrin blocking substance, including but not limited to an anti-progastrin antibody, particularly a chimeric human/non-human antibody, a humanized or a fully human monoclonal anti-progastrin antibody, or any other molecule that is functional in binding progastrin.

The present invention also provides compositions, methods and kits for screening samples suspected of containing progastrin. Such screening may be performed on patient samples, or laboratory samples suspected of containing or producing such a polypeptide. A kit can contain an antibody of the present invention. The kit can contain a suitable buffer and reagents for detecting an interaction between a sample and antibody of the present invention. The provided reagent can be radiolabeled, fluorescently-labeled or enzymatically-labeled agent capable of binding or interacting with an antibody of the present invention.

The reagent of the kit can be provided as a liquid solution, attached to a solid support or as a dried powder. When the reagent is provided in a liquid solution, preferably, the liquid solution is an aqueous solution. Preferably, when the reagent provided is attached to a solid support, the solid support can be chromatographic media, a test plate having a plurality of wells, or a microscope slide. When the reagent provided is a dry powder, the powder can be reconstituted by the addition of a suitable solvent, which may be provided.

The kit of the invention is provided in a container that generally includes a vial into which the antibody, antigen or detection reagent may be placed, and preferably suitably aliquotted. The kits of the present invention will also typically include a means for containing the antibody, antigen, and reagent containers for commercial sale. Such containers may include plastic containers into which the desired vials are retained and one or more necessary chemicals, such as chromatography material, solvents and eluents, test tubes, detergents, antibodies and chemicals for the detection reaction.

In still further embodiments, the present invention concerns immunodetection methods and associated kits. It is proposed that progastrin or peptide fragments thereof may be employed to detect antibodies having reactivity therewith, or, alternatively, antibodies prepared in accordance with the present invention, may be employed to detect progastrin, progastrin-mimic molecules or progastrin epitope-containing peptides. In general, these methods will include first obtaining a sample suspected of containing such a precursor, peptide or antibody, contacting the sample with an antibody or peptide in accordance with the present invention, under conditions effective to allow the formation of an immunocomplex, and then detecting the presence of the immunocomplex.

A wide variety of methods of detection of immunocomplex formation are well known in the art, for example, ELISA, RIA, immunoblot (e.g., dot blot, slot blot, western blot etc.), indirect immunofluorescence techniques and methods that rely on detection of changes in physical parameters, such as for instance, surface plasmon resonance and the like. In one widely used method immunocomplex formation is detected through the use of a label, such as a radiolabel or an enzyme tag (such as alkaline phosphatase, or horseradish peroxidase). Additional advantages may accrue through the use of a secondary binding ligand such as a second antibody or an avidin-coupled molecule for binding a biotinylated ligand, according to methods well known in the art.

EXAMPLES

Example 1

Production of MAbs to the N-terminal End of Human Progastrin

The peptide, SWKPRSQQPPC ("hProGastrin (1-9)-PC", SEQ ID NO: 16) containing the amino acid sequence 1-9: SWKPRSQQP (SEQ ID NO: 17) of human progastrin, forming the N-terminal end epitope of human progastrin, followed by the linker sequence -Pro-Cys-, was synthesized commercially by standard solid phase peptide synthesis methodology.

The peptide was incorporated into an immunogen to induce antibodies to the N-terminus of human progastrin as follows: The peptide was first covalently linked to diphtheria toxoid ("DT") to yield a peptide-carrier conjugate. The number of peptide units substituted on each DT carrier was determined and finally, the conjugate was formulated as an immunogen. The techniques used were as described in U.S. Pat. No. 5,622,702 to Gevas et al.

Briefly, the peptide was chemically conjugated to the carrier with the heterobifunctional cross-linker, epsilon-maleimidocaproic acid N-hydroxysuccinimide (ε-MCS). The conjugate was purified by dialysis against 0.1 M sodium phosphate buffered saline, pH 7.3 (PBS) and the protein concentration determined by the Lowry assay. The substitution level of peptide on DT (14.7 peptides per 100,000 Da molecular weight of DT) was determined on a molar basis by amino acid analysis of the conjugate. The dissolved conjugate was then formulated as an immunogen with Montanide ISA 703 (SEPPIC, France) as adjuvant by mixing the conjugate solution with the Montanide ISA 703 oil at a 30/70 ratio (wt/wt of conjugate solution/adjuvant). Mixing was achieved by drawing the appropriate volumes of each liquid into a syringe and then rapidly passing the solutions back and forth between this and a second syringe through an inter-locking hub.

Mice were initially immunized by i.p. injection with 0.1 mg of the peptide-DT conjugate immunogen/Montanide ISA 703 in a volume of 0.1 mL. A second injection of an identical dose was given three weeks after the first injection.

To create hybridomas producing a MAb selective for the N-terminus of human progastrin, spleen cells from the immunized mice were fused with a standard mouse myeloma fusion partner cell line by standard techniques well known to those skilled in the art. See, for instance, U.S. Pat. No. 4,196,265 *Method of producing antibodies* to Kaprowski et al; "Selected Methods in Cellular Immunology" (Chapter 17: *Immunoglobulin Producing Hybrid Cell Lines*, B. Mishell and S. Shiigi, W. H. Freeman and Co., San Francisco, 1980); Harlowe and Lane, *Antibodies: A Laboratory Manual*, Cold Spring Harbor Laboratory Press, 1988; Zola, *Monoclonal Antibodies: A Manual of Techniques*, CRC Press, Inc., Boca Raton, Fla., 1987. Immunized mice were boosted with an i.p. injection of 0.1 mg of the above-described peptide-DT conjugate in PBS 4 days prior to collection of their spleen cells for the cell fusion. Initial selection of hybrid cells was done using hypoxanthine-aminopterin-thymidine supplemented media, as described in Mishell and Shiigi. This fusion was designated F490.

The first selection step for isolating hybridomas producing MAbs to the N-terminal end of human progastrin was selection of cells for production of antibody to the target peptide and for stability of the hybrid cell lines. The selection of cells producing antibody was accomplished by screening cell culture media obtained from tissue culture wells containing single clones for antibody to the N-terminal end of human progastrin. The screening was by means of an ELISA using as target antigen a conjugate of the synthetic peptide hProGastrin(1-9)-PC linked through the terminal cysteine-11 to bovine serum albumin (BSA) as an immunological carrier. Suitable ELISA techniques are known to those skilled in the art, several examples of which are listed below. Stable cell lines were obtained by twice cloning each hybrid that produced antibodies that bound the hProGastrin(1-9)-PC-BSA conjugate in the ELISA test. By these methods, eight hybrid cell lines were obtained that produced MAbs to the N-terminal end of human progastrin. These hybrid lines were designated: 490-1; 490-2, 490-3; 490-4, 490-5; 490-6, 490-7 and 490-8.

Example 2

Production of MAbs to the N-terminal region of Human Progastrin

The peptide, SQQPDAPLGPPC ("hProGastrin(6-14)-PPC". SEQ ID NO: 18) containing the amino acid sequence 6-14 SQQPDAPLG (SEQ ID NO: 19) of human progastrin, forming an N-terminal region epitope of human progastrin, followed by the linker sequence -PPC, was synthesized commercially by standard solid phase peptide synthesis methodology.

The SQQPDAPLGPPC peptide (SEQ ID NO: 18) was incorporated into an immunogen to induce antibodies to the N-terminal region of human progastrin as described in Example 1 above. Immunization and isolation of a fusion designated F491 was also performed as described above.

The selection of hybridomas producing MAbs to the N-terminal region of human progastrin was accomplished by screening cell culture media obtained from tissue culture wells containing single clones for antibody to the N-terminal region of human progastrin. Screening was by an ELISA using as target antigen a conjugate comprising the synthetic peptide hProGastrin(6-14)-PPC, linked through cysteine-12 to bovine serum albumin (BSA) as an immunological carrier. Stable cell lines were obtained by twice cloning each hybrid that produced antibodies that bound the hProGastrin(6-14)-PPC-BSA conjugate in the ELISA. Three hybrid cell lines were obtained that produced MAbs to the N-terminal region of human progastrin. These hybrid cell lines were designated: 491-1, 491-2 and 491-3.

Example 3

Production of MAbs to the C-Terminal End of Human Progastrin

The peptide, CPPGRRSAEDEN ("hProGastrin(72-80)-PPC". SEQ ID NO: 20) having the amino acid sequence 72-80 GRRSAEDEN (SEQ ID NO: 21) of human progastrin at the C-terminal end preceded by the linker sequence CPP-, was synthesized commercially by standard solid phase peptide synthesis methodology. The peptide was incorporated into an immunogen to induce antibodies to the C-terminus of human progastrin as described in Examples 1 and 2 above.

Mice were initially immunized by i.p. injection with 0.1 mg of the peptide-DT conjugate immunogen/Montanide ISA 703 in a volume of 0.1 mL. A second injection of an identical dose was given three weeks after the first injection.

To create hybridomas producing a MAb selective for the C-terminus of human progastrin, spleen cells from the immunized mice were fused with a standard mouse myeloma fusion partner cell line by standard techniques as described above to produce the fusion designated F495.

The first selection step for isolating hybridomas producing MAbs to the C-terminal end of human progastrin was selection of cells for production of antibody to the target peptide and for stability of the hybrid cell lines. The selection of cells producing antibody was accomplished by screening cell culture media obtained from tissue culture wells containing single clones for antibody to the C-terminal end of human progastrin. The screening was accomplished by means of an ELISA using as target antigen a conjugate comprising the synthetic peptide hProGastrin(72-80)-PPC, linked through cysteine-1 to bovine serum albumin (BSA) as an immunological carrier. Stable cell lines were obtained by twice cloning each hybrid that produced antibodies that bound the hProGastrin(72-80)-PPC-BSA conjugate in the ELISA. Four hybrid cell lines were obtained that produced MAbs to the C-terminal end of human progastrin. These hybrid lines were designated: 495-1; 495-2, 495-3 and 495-4.

Example 4

ELISA Titers of Antibodies to Specific Regions of Progastrin

The purpose of this analytical method is to detect and to determine the titer of anti-progastrin antibodies in test samples by ELISA. The anti-progastrin antibody ELISA of the invention is based upon the specific binding of antibodies (which may be polyclonal antibodies or monoclonal antibodies) to a progastrin peptide-BSA conjugate. Binding of the peptide in the ELISA confirms that the antibody specifically binds a progastrin epitope within the progastrin peptide sequence of the conjugate.

The progastrin-BSA conjugates tested included the three conjugates listed in Examples 1, 2 and 3: hProGastrin(1-9)-PC-BSA; hProGastrin(6-14)-PPC-BSA; and hProGastrin(72-80)-PPC-BSA (respectively). The conjugates were prepared using the same progastrin peptides used to make the DT-linked immunogens, using the cross-linking reagent ε-MCS, as described above.

In the first step of the ELISA, conjugate was bound to the wells of a 96 well ELISA plate. Free conjugate was removed by a wash step using a 96 well plate washer. The test (or control) antiserum was then added. Anti-progastrin Ab present in the test serum bound to the conjugate by virtue of progastrin peptide epitopes present on the antigen. Bound antibodies were then detected by the addition of an anti-IgG-Alkaline Phosphatase reagent, which is species specific for the anti-progastrin antibodies being detected. For example, mouse anti-progastrin antibodies were detected using Rabbit anti-Mouse IgG-Alkaline Phosphatase conjugate ("RAM-AP"), which binds to the mouse anti-progastrin Ab, as the Ab detection reagent. The AP moiety of anti-Ig-AP conjugate subsequently catalyses conversion of substrate to a colored product (p-nitrophenol). Color development was measured as absorbance at 405 nm in an ELISA plate reader.

Pooled mouse anti-progastrin serum (collected from the mice immunized for the production of anti-progastrin hybridomas) or ascites fluid containing mouse anti-progastrin MAb was used as positive control for ELISAs targeting the progastrin epitope that was used to induce the antibodies. Serum from the same animal species as the test sample was used as negative control (e.g., normal sera, or pre-immune sera, etc.).

The magnitude of color development in the linear range was directly proportional to the quantity of anti-progastrin Ab bound to the target antigen. A plot of the dilution series of the positive standard (anti-progastrin) serum versus absorbance values was used to generate binding curves. The anti-progastrin Ab titers of the test samples were then determined from the greatest dilution that produces an absorbance that can be distinguished from the absorbance obtained with the same dilution of negative control (limiting dilution analysis).

Reagent Solutions: The quantities of reagents and solutions specified for preparation in this analytical method were chosen for convenience only and are provided as examples, and are not to be taken as limitations. The actual quantities can be scaled according to requirements.

1. Carbonate buffer with 0.02% $NaN_3$ ("Carbonate buffer") was prepared by dissolving 1.59 g $Na_2CO_3$ and 2.93 g $NaHCO_3$ in approximately 750 ml of distilled water and stirring with a magnetic stirrer. 4 ml of 5% $NaN_3$ solution was added and stirred. The solution was adjusted to 1.0 liter with water. The pH was measured, (this should be 9.6±0.2) and adjusted with 1.0 M NaOH or 1.0 M HCl if necessary). The buffer was stored in a refrigerator until needed.
2. FTA (PBS) with 0.05% Tween-20 and 0.02% $NaN_3$ ("FTA/Tween") was prepared by dissolving 9.23 g FTA in approximately 750 ml of purified water. 0.5 ml Tween-20 and 4 ml 5% $NaN_3$ was added and adjusted to 1.000 liter with water.
3. 1% BSA in FTA/Tween ("BSA/FTA/Tween") was prepared by dissolving 10 g BSA in 1000 ml FTA/Tween.
4. Substrate buffer: 50 mg $MgCl_2.6H20$ was dissolved in 448 ml of purified water. 50 ml of DEA and 2 ml 5% $NaN_3$ were added and the pH adjusted to 9.8 with concentrated HCl. The buffer was stored protected from light at room temperature.
5. PBS, pH 7.2: Was prepared from solid FTA (FTA Hemagglutination Buffer ("FTA") (Becton Dickenson Microbiology Systems, Cockeysville, Md.)).

Elisa Procedure: Coating with Antigen: A solution of 1 μg/ml progastrin-BSA conjugate target antigen (described above), in Carbonate buffer was prepared. A minimum of 5.2 ml of antigen solution was needed for each plate to be coated. Antigen solution is prepared by making a 1:1000 dilution of the 1 mg/ml conjugate stock solution with Carbonate buffer. Plates may be any plate suitable for ELISA assays, such as for instance, Microtiter® Immunoassay Plates, rigid styrene (e.g., Immulon® 2 "U" bottom 96 well plates, Dynatech Laboratories, Inc., VA; or Flat-bottom 96 well plates, polystyrene: e.g., Microwell Plates, NUNC, vendor VWR). Immulon® 2 "U" bottom plates are coated with antigen by adding 50 μl/well of the antigen solution. Plates were stored in a moist chamber (e.g., a closed container with a moist paper towel) to prevent moisture loss and incubated overnight in the refrigerator (at 2°-8° C.).

Preparation of Serum Dilutions: Any convenient dilution series is acceptable. For example, $1/10^{0.5}$ serial dilution series of the positive standard and negative control and test sera were used as shown in Table 1. Samples were diluted in BSA/FTA/Tween solution in flat bottom 96 well plates (12-channel multipipettors enable simultaneous dilution of up to 12 sera).

TABLE 1

Serial dilutions starting at 1:1000 were prepared as shown

| 96 well plate Row # | Serum Dilution | Titer[1] (=1/Dilution) |
|---|---|---|
| A | $1:1,000 = 10^{-3}$ | $10^3$ |
| B | $1:3,162 = 3.16 \times 10^{-4} = 10^{-3.5}$ | $3.16 \times 10^3$ |
| C | $1:10,000 = 10^{-4}$ | $10^4$ |
| D | $1:31,623 = 3.16 \times 10^{-5} = 10^{-4.5}$ | $3.16 \times 10^4$ |
| E | $1:100,000 = 10^{-5}$ | $10^5$ |
| F | $1:316,230 = 3.16 \times 10^{-6} = 10^{-5.5}$ | $3.16 \times 10^5$ |
| G | $1:1,000,000 = 10^{-6}$ | $10^6$ |
| H | $1:3,163,300 = 3.16 \times 10^{-7} = 10^{-6.5}$ | $3.16 \times 10^6$ |

[1]The titer of each dilution is calculated as the reciprocal of the dilution.

A sufficient volume of a dilution of each sample was prepared to provide a minimum working volume of 200 μl. Depending on the sample titer, dilutions beginning with a 1/100 (for low titer sample) or 1/1000 (for high titer sample) dilution of each sample in row A were made, then proceeding with serial dilutions down each column to row H (See Table 1), yielding a total of eight dilutions of each sample. The dilution series of the negative control was prepared beginning at 1/100. Samples of the dilution series of the positive standard antibody and the prebleed/negative control antibody were run in duplicate on each plate.

PLATE WASHING: Using the plate washing, (e.g., Ultrawash Plus; or, DynaWasher II (Dynatech Laboratories, Inc., Va.) or equivalent) the coated plates were washed four times each with FTA/Tween and then "slapped" the plates on paper towels to remove residual solution.

Antibody Binding: Following the sample plate dilution series as shown in Table 2 below, 50 μl/well of the diluted sample was transferred to the corresponding wells of the antigen coated "U" plates. The plates were incubated in a moist chamber for 1 hour at room temperature.

TABLE 2

EXAMPLE OF A 96 WELL PLATE ELISA SETUP

|   | 1 | 2 | 3 | 4 | 5 | 6 | 7 | 8 | 9 | 10 | 11 | 12 | Sample Dilution |
|---|---|---|---|---|---|---|---|---|---|----|----|----|-----------------|
| A | Neg. | Neg. | Pos. | Pos. | TS 1 | TS 2 | TS 3 | TS 4 | TS 5 | TS 6 | TS 7 | TS 8 | $10^{-3}$ |
| B | Neg. | Neg. | Pos. | Pos. | TS 1 | TS 2 | TS 3 | TS 4 | TS 5 | TS 6 | TS 7 | TS 8 | $10^{-3.5}$ |
| C | Neg. | Neg. | Pos. | Pos. | TS 1 | TS 2 | TS 3 | TS 4 | TS 5 | TS 6 | TS 7 | TS 8 | $10^{-4}$ |
| D | Neg. | Neg. | Pos. | Pos. | TS 1 | TS 2 | TS 3 | TS 4 | TS 5 | TS 6 | TS 7 | TS 8 | $10^{-4.5}$ |
| E | Neg. | Neg. | Pos. | Pos. | TS 1 | TS 2 | TS 3 | TS 4 | TS 5 | TS 6 | TS 7 | TS 8 | $10^{-5}$ |
| F | Neg. | Neg. | Pos. | Pos. | TS 1 | TS 2 | TS 3 | TS 4 | TS 5 | TS 6 | TS 7 | TS 8 | $10^{-5.5}$ |
| G | Neg. | Neg. | Pos. | Pos. | TS 1 | TS 2 | TS 3 | TS 4 | TS 5 | TS 6 | TS 7 | TS 8 | $10^{-6}$ |
| H | Neg. | Neg. | Pos. | Pos. | TS 1 | TS 2 | TS 3 | TS 4 | TS 5 | TS 6 | TS 7 | TS 8 | $10^{-6.5}$ |

Abbreviations:
Pos. = Positive standard sample;
Neg. = Prebleed/negative control sample;
TS 1-TS 8 = Test samples Antibody Detection Reagent: An appropriate dilution of Anti-Ig-Alkaline Phosphatase Conjugate was prepared in FTA/Tween. A minimum of 5.2 ml per plate in the assay was required. Plates were washed as described above. 50 µl/well of the RAM-AP solution (Anti-Ig-Alkaline Phosphatase Conjugate e.g., for testing mouse anti-progastrin antibodies, Rabbit anti-Mouse IgG (H+L)-Alkaline Phosphatase (Zymed)) was added to every well in the "U" plate and incubated at room temperature in the moist chamber for 1 hour.

To detect anti-progastrin antibodies in serum obtained from species other than mouse, an anti-Ig-AP conjugate must be used that is specific for the species that produced the test serum (e.g., human anti-progastrin antibodies are detected with an anti-human IgG-AP reagent, used at the dilution established for each lot of reagent). The positive standard and negative control serum should be obtained from the same species as the test serum.

Substrate Solution: p-NPP tablets (p-nitrophenylphosphate, supplied as Phosphatase Substrate Tablets, Sigma 104 ("p-NPP") (Sigma Chemical Co., St. Louis, Mo.)) were removed from the freezer and allowed to warm to room temperature. Immediately before use, a 1 mg/ml solution of p-NPP was prepared by adding one tablet of p-NPP to 5 ml of DEA substrate buffer at room temperature. Each 5-ml aliquot of substrate solution was sufficient for one assay plate. Substrate solution was stored in the dark until used.

Substrate Addition: Plates were washed as described above. To all wells, beginning with column 1, 50 µl/well of p-NPP solution was simultaneously added with an 8 (or 12) channel multipipettor beginning with row A.

Monitoring Reaction: The development of the substrate solution was stopped after 10-15 minutes.

Stop Reaction: The reaction was stopped by adding 50 µl of 1.0 M NaOH to each well with the 8 (or 12) channel pipettor. The NaOH solution was added to the wells in the same order, and with the same timing, as the substrate solution was added. The reagents were gently mixed by carefully shaking the plate on the counter top.

Measure Absorbance: The entire plate was read with an ELISA reader. The ELISA reader was set to measure at $A_{405\ nm}$ for p-nitrophenol.

Data Analysis: The antibody titer of each serum was determined as follows: The absorbance obtained for each sample was plotted on the ordinate (linear scale) against (1/dilution) on the abscissa (log scale) for each serum, including the positive standard, on a semi-log graph scale. By plotting the inverse of the dilution, the titer could be read directly on the X-axis. Occasionally, an absorbance value was clearly off the binding curve for a particular serum (outlier points); such values were excluded from the curve. The titer of each serum is determined as the final dilution of test antibody that can be distinguished from the same dilution of negative control sample, based upon absorbance values. Generally, the limit of differentiation between the two results is an absorbance of 0.25 absorbance units or more (depending on sample to sample variability in the assay).

Example 5

Determination of Antibody Specificity by Inhibition ELISA

The same method as in the Example above is followed for the peptide inhibition ELISA with the exceptions described below.

Preparation of Inhibitor: The appropriate target hormone peptide, in this case peptide(s) expressing progastrin epitope(s), were prepared as working stocks of 1 µmol/ml (1000 µM). The inhibition dilution series was prepared from the working stock solution, at dilution ratios from 1:2 to 1:10, yielding a total of 8 or 12 dilutions depending on the layout on the plate.

Preparation of Sample Dilution: A series of titrations of the sample were done prior to the inhibition assay to establish the dilution of the antibody sample at 50% maximal binding. The sample was then prepared to 2× the 50% binding concentration, for mixing with equal volumes of peptide inhibitor and with buffer as a control in the inhibition assay. The sample mixture was incubated in a moist chamber for approximately 30 minutes and then added to the washed coated ELISA plate and incubated for approximately 1 hour in a humidity chamber. The percent binding was determined from the absorbance readings (subtracted from the background) by dividing the absorbance obtained from the sample with inhibitor by the absorbance obtained from the sample control without inhibitor, and multiplying this value by 100. Finally, the percent inhibition was determined by subtracting the percent binding from 100%.

The test samples for use in this assay can be serum, MAb in cell culture supernatant, ascites fluid, or affinity-purified antibody (Ab). For Abs against target antigens other than the amino terminus of progastrin, the appropriate target hormone antigen and inhibitor are used. An unrelated peptide inhibitor should be included as a negative control.

Example 6

Anti-progastrin MAb for Isotype and Specificity by ELISA

The anti-progastrin MAb described in Example 1 (F490), Example 2 (F491) and Example 3 (F495) were characterized for isotype and specificity by ELISA. The target antigen for each MAb was the same as that described in Examples 1 through 3. Thus, MAb from fusion 490 were tested against hProGastrin(1-9)-PC-BSA; MAb from fusion 491 were tested against hProGastrin(6-14)-PPC-BSA; and, MAb from fusion 495 were tested against hProGastrin(72-80)-PPC-BSA. Isotypes were determined by the method of Example 4, wherein the secondary rabbit anti-mouse Ig reagents were specific for mouse antibody isotypes. Specificity was determined by the method of Example 5, using the following peptides as inhibitors: hProGastrin(1-9)-PC, hProGastrin(6-14)-PPC, hProGastrin(72-80)-PPC, human G17, human G34, human G17-Glycine extended and luteinizing hormone releasing hormone (LHRH) as a negative control.

The results of these tests are given in Table 3. As the Table shows, all of the MAb were of the IgGI subclass, with the exception of antibodies 491-2 and 495-2, both of which were of the IgG2a subclass. The Table also shows that each of the individual MAbs was specific for the epitope used for immunization. Thus, all of the 490 series MAbs were specific for the progastrin epitope sequence 1-9; all of the 491 series MAbs were specific for the progastrin epitope sequence 6-14; and, all of the 495 series MAbs were specific for the progastrin epitope sequence 72-80. These MAb are deemed suitable for tests designed to detect and measure progastrin in biological test samples consisting either of fluids (e.g., plasma, lymph, ascites, saliva, etc.) and in tissue specimens, (e.g., biopsy specimens of normal tissue or tumor origin, or of shed cells from such tissues, etc.).

The synthesis methods employed were those in common commercial usage and are well known to those skilled in the art. Progastrin SRS 1 was synthesized for use in an assay to detect and quantify human progastrin 1-80.

The progastrin SRS 1 peptide had the following structure: [progastrin 1-9-(PGGPP)-progastrin 72-80]. The amino acid sequence of the peptide was: SWKPRSQQPPGGPPGRRSAEDEN (SEQ ID NO: 14). The mass of this peptide was 2535.1, and the purity of this peptide was greater than 90% when tested by HPLC.

Progastrin SRS 2 was synthesized for use in an assay to detect and quantify human progastrin 6-80. The progastrin SRS 2 peptide had the following structure: [progastrin 6-14-(PPGGPP)-progastrin 72-80]. The amino acid sequence of the peptide was: SQQPDAPLGPPGGPPGRRSAEDEN (SEQ ID NO: 15). The mass of this peptide was 2432.4, and the purity of this peptide was greater than 90% when tested by HPLC.

Example 8

Immunoenzymometric Assay Utilizing Anti-Progastrin MAb and Progastrin SRS Peptides to Measure Progastrin The following analytical methods (immunoenzymometric assay) were used to determine free (non-complexed) human progastrin 1-80 or human progastrin 6-80 present in biological fluids such as human plasma, by using monoclonal and/or polyclonal antibodies directed to the N-terminus or the C-terminus of the particular molecular form of progastrin that is being assayed. Alternatively, a combination of a polyclonal antibody directed to the N-terminus or to the C-terminus of the molecule can be used in combination with a monoclonal antibody directed to the C-terminus or to the N-terminus of the molecule respectively.

TABLE 3

Characterization of MAbs from Fusions 490, 491 and 495.

| | | | | Percent Inhibition with 25 micromolar Peptide | | | | | | |
|---|---|---|---|---|---|---|---|---|---|---|
| Specificity | MAb | Endpoint Titer | Antibody Subclass | ProG 1-9 | ProG 6-14 | ProG 72-80 | G17 | G17-gly | G34 | LHRH |
| Progastrin 1-9 (N terminal end) | 490-1 | 30,000 | IgG1 | 100 | 0 | 0 | 0 | 0 | 0 | 0 |
| | 490-2 | 30,000 | IgG1 | 100 | 0 | 0 | 0 | 0 | 0 | 0 |
| | 490-3 | 30,000 | IgG1 | 100 | 0 | 0 | 0 | 0 | 0 | 0 |
| | 490-4 | 30,000 | IgG1 | 100 | 0 | 0 | 0 | 0 | 0 | 0 |
| | 490-5 | 10,000 | IgG1 | 100 | 0 | 0 | 0 | 0 | 0 | 0 |
| | 490-6 | 10,000 | IgG1 | 100 | 0 | 0 | 0 | 0 | 0 | 0 |
| | 490-7 | 10,000 | IgG1 | 100 | 0 | 0 | 0 | 0 | 0 | 0 |
| | 490-8 | 10,000 | IgG1 | 100 | 0 | 0 | 0 | 0 | 0 | 0 |
| Progastrin 6-14 (N term region) | 491-1 | >30,000 | IgG1 | 0 | 100 | 0 | 0 | 0 | 0 | 0 |
| | 491-2 | 10,000 | IgG2a | 0 | 100 | 0 | 0 | 0 | 0 | 0 |
| | 491-3 | 1,000 | IgG1 | 0 | 100 | 0 | 0 | 0 | 0 | 0 |
| Progastrin 72-80 (C terminal end) | 495-1 | 30,000 | IgG1 | 0 | 0 | 100 | 0 | 0 | 0 | 0 |
| | 495-2 | 30,000 | IgG2a | 0 | 0 | 100 | 0 | 0 | 0 | 0 |
| | 495-3 | 30,000 | IgG1 | 0 | 0 | 100 | 0 | 0 | 0 | 0 |
| | 495-4 | 10,000 | IgG1 | 0 | 0 | 100 | 0 | 0 | 0 | 0 |

Example 7

Synthesis of Progastrin Surrogate Reference Standards (SRS) for Measurement of Progastrin by Immunoassay To demonstrate the utility of SRS, two progastrin SRS peptides were synthesized by solid phase peptide synthesis.

1. Plate Coating: Antibody selective for the N terminus of the particular human progastrin molecular form to be tested was coated at an optimal concentration onto the surface of the micro wells of a test plate. NUNC Maxisorp, F 96 ELISA plate (cat. No. 439454) test plates were used and the antibody coating solution is prepared in sodium borate buffer (20 mM, pH 8.0, containing 0.1% sodium azide). The concentration of affinity purified Mab in the coating solution was preferably about 5 μg/mL. 100 μL of Mab solution is added per well, and coating was allowed to proceed overnight at 4° C. in a humidified sealed box. Plates were coated with affinity purified 490-1 Mab for the detection of progastrin 1-80, using SRS 1 to establish a standard curve in the assay. Plates were coated with affinity purified 491-1 Mab for the detection of progastrin 6-80, using SRS 2 to establish a standard curve in the assay.

2. Plate washing: The coating solution were removed and wash buffer (approx. 400 μl per well) was added and then removed. This wash cycle was repeated as many times as required; generally, three or four washes total. Wash buffer was 0.010 M phosphate buffer; 0.0027 M potassium chloride and 0.137 M sodium chloride, pH 7.4, containing 0.01% w/v Triton X-100). Plate washing may be automated.

3. Plate blocking: Blocking buffer containing protein and detergent (1% BSA/0.1% Triton X-100 in coating buffer) was added to the micro wells (200 μL/well), and the plates were incubated for 1 hour at room temperature in a humidified box. Plates were stored refrigerated at approximately 4° C. in this form.

4. Sample and standard addition: Plates were washed as described above. Reference standards (such as, for instance, SRS 1, SRS 2, or authentic progastrin forms; or, negative control peptide such as Gastrin 17) were prepared as dilution series to generate standard curves. In the tests of this example, SRS 1 and 2 were prepared at a concentration of 10 μM, and diluted to 100 fM in 1:10 dilution series. The standards and test samples were prepared in assay buffer (1% BSA, 0.1% bovine γ-globulin prepared in wash buffer). The solutions were then added to each well (100 μL/well). The reaction was allowed to proceed for 2 hours at room temperature in a humidified box.

The optimal antigen concentration was determined by generating a standard curve using known concentrations of progastrin SRS of the form to be assayed, the standard curve having the required sensitivity and precision over the required useful concentration range. For progastrin (either 1-80 or 6-80), the useful progastrin concentration range of the assay was generally from background (about 1 pM or less) to about 100 nM. Greater accuracy can be achieved by using a narrower dilution series of reference standard, such as a 1:2 dilution series.

It will be immediately recognized that assay sensitivity and precision can be readily modified or enhanced by alteration of other assay parameters, such as the selection of the particular Mab for well coating or for enzyme labelling, the concentrations of reagents, the composition of buffers, the selection of enzyme-substrate systems, the incubation times, and other parameters that can be modified to suit the requirements of the assay. The appropriate sensitivity and precision over the required range can be readily determined by those of ordinary skill in the art without undue experimentation.

5. Addition of conjugate: Following washing, assay buffer containing monoclonal or polyclonal antibody specific for the C-terminus of the progastrin form to be assayed (conjugated with an enzyme label), was added to each well. In the case of this example, MAbs against the C-terminal end of progastrin were affinity purified then coupled to horse radish peroxidase (HRP). The MAbs were shown to retain binding to the C terminal end of progastrin and to have HRP activity. Separate conjugates were made with each of the four Mabs 458-1 through 458-4. For the purposes of this test, the conjugates were used separately and not mixed. The conjugates were used at a 1:2000 dilution of the stock solution of 630 μg/mL, and 100μ was added per well. The reaction was allowed to proceed at room temperature (nominally +22° C.) for at least 1 hour.

6. Addition of substrate: The wells were washed as described above, and 100 μL of TMB Solution (Pierce) substrate solution was added to each well. Reactions were allowed to proceed for 30 minutes, then 100 μL of stop solution of 0.2 M $H_2SO_4$ is added to each well. Examples of suitable enzyme substrates for use in development of the detection compound include nitro-phenylphosphate for alkaline phosphatase or tetramethylbenzidine sulfonate (TMBS) for horseradish peroxidase. The degree of color development, read as Absorbance Units (AU, read at 450 nm in the case of TNBS, or at 405 nm in the case of p-nitrophenol) is indicative of the amount of progastrin present in the test sample, and the actual concentration can be determined by reading absorbance of the test sample against a standard curve generated with known concentrations of SRS or against a standard curve generated with authentic progastrin.

7. Reading: When sufficient assay signal was attained the signal was measured using a microplate reader/spectrophotometer.

8. Data Processing: The assay signals obtained with known standard solutions of the SRS (or progastrin) form were used to construct a calibration curve (signal vs. concentration). The calibration curve was used to interpolate concentrations of the gastrin hormone form in test samples.

Example 9

Immunoenzymometric Assay Designed to Measure Progastrin 1-80

The results of the assay for progastrin 1-80 are shown in Table 4. The general methods for this assay are described in Example 8. In this test, wells were coated with affinity purified Mab 490-1, specific for the N terminal end of progastrin. The detection conjugate used was Mab 495-1-HRP conjugate. As the data show, SRS 1 was detected at concentrations down to 100 pM; whereas the closely related SRS 2 was detected only to 100 nM. Therefore, the working range of this assay for progastrin 1-80 would be below 100 nM, and above 10 pM. The negative control peptide Gastrin 17 was not detected. This example demonstrates that the progastrin Mab can be used to assay for progastrin 1-80. This example also demonstrates the utility of SRS 1 as a standard molecule for measuring progastrin 1-80 by ELISA.

TABLE 4

Assay for progastrin 1-80.

| Peptide Concentration | Absorbance Values (background subtracted) | | |
|---|---|---|---|
| | SRS 1 | SRS 2 | Gastrin 17 |
| 10 μM | NT | 0.942 | NT |
| 1 μM | NT | 0.955 | NT |
| 100 nM | 0.951 | 0.109 | 0.001 |
| 10 nM | 1.079 | 0 | 0.001 |
| 1 nM | 0.923 | 0 | 0.002 |
| 100 pM | 0.094 | 0.002 | 0 |
| 10 pM | 0.005 | 0.002 | 0 |
| 1 pM | 0 | NT | 0.001 |
| 100 fM | 0 | NT | 0.015 |

Example 10

Immunoenzymometric Assay Designed to Measure Progastrin 6-80

The results of the assay for progastrin 6-80 are shown in Table 5. The general methods for this assay are described in Example 8. In this test, wells were coated with affinity purified Mab 491-1, specific for the N terminal region of progastrin (amino acids 6-14). The detection conjugate used was Mab 495-1-HRP conjugate. As the data show, SRS 2 was detected at concentrations down to 100 pM (as the absorbance at this concentration was above baseline, the assay could detect less than 100 pM); whereas the closely related SRS 1 was detected only to 100 μM. Therefore, the working range of this assay for progastrin 6-80 would be below 100 μM, and above 10 pM. The negative control peptide Gastrin 17 was not detected. This example demonstrates that the progastrin Mab can be used to assay for progastrin 6-80. This example also demonstrates the utility of SRS 2 for measuring progastrin 6-80.

TABLE 5

Assay for progastrin 6-80.

| Peptide Concentration | Absorbance Values (background subtracted) | | |
|---|---|---|---|
| | SRS 1 | SRS 2 | Gastrin 17 |
| 100 μM | 0.191 | 3.407 | 0.002 |
| 10 μM | 0.015 | 2.324 | 0.002 |
| 1 μM | 0.010 | 2.721 | 0.002 |
| 100 nM | 0.010 | 1.856 | 0.002 |
| 10 nM | 0.008 | 1.431 | 0.001 |
| 1 nM | 0.009 | 0.462 | 0.013 |
| 100 pM | 0.004 | 0.053 | 0 |
| 10 pM | 0 | NT | 0.001 |
| 1 pM | 0 | NT | 0.015 |

NT: Not tested.

Example 11

Selection of Optimal Mab for Specific Applications

Despite sharing specificity for a given epitope, different Mabs against a given epitope may differ in their performance in specific applications. Thus, the Mabs must be compared for their activity in each circumstance, in order that the MAb with optimal performance be selected for use in a particular application. This example demonstrates how MAbs specific for the C terminal end of progastrin differ in their ability to serve as progastrin detection antibodies in the immunoenzymometric assay for progastrin and provide an optimal formulation.

The detection antibody reagent in the quantitative assay for progastrin (described in Example 8) is a Mab directed against the C terminal end epitope of progastrin linked to HRP. Four Mabs specific for the C terminal end epitope of progastrin were isolated by cloning from fusion number 495, described above. These were Mabs 495-1, 495-2, 495-3 and 495-4. To prepare HRP conjugates of these MAbs, we followed methodologies familiar to those skilled in the art, by employing our unique components in conjunction with commercially available kits at key steps. Thus, each of MAb 495-1 through -4 were separately produced as ascites MAbs in mice (as described in Mishell and Shiigi, chapter 17). The presence of a MAb in the ascites fluid was confirmed by direct binding ELISA against the target antigen hProGastrin(72-80)-PPC-BSA, as described above.

MAbs were affinity purified from the ascites fluid by column chromatography over hProGastrin(72-80)-PPC linked to sulfolink gel (Pierce) and eluted with glycine buffer, following the directions supplied with the Pierce Sulfolink Kit. Mabs were further purified by diafiltration in an Amicon filtration unit, and the final protein concentration was determined by $A_{280}$ measurement. Each of the four purified MAb preparations was conjugated to HRP using the Pierce EZ-Link™ Plus kit. After purification, the HRP and antigen binding activity of each Mab-HRP conjugate was checked by direct binding ELISA against the hProGastrin(72-80)-PPC-BSA target antigen, and all were found to be active. Final concentrations of the four conjugates were set at 0.63 to 0.68 mg/mL.

To compare the performance of the four MAb-HRP conjugates in the immunoenzymometric assay for progastrin, the assay was run as described in Example 9 using SRS 1 and in Example 10 using SRS 2. Each of the 495 MAb-HRP conjugates were tested separately in each of the individual assays, as detection reagents for captured SRS 1 and 2. The MAb-HRP conjugates were used at 1:2000 dilutions from the stock solutions. In the assay to detect SRS 2 (for progastrin 6-80), wherein the plate was coated with MAb 491-1 and SRS 2 was thereby captured, the optimal conjugate for detection of the captured SRS 2 was 495-1-HRP. This can be seen in Table 6, wherein 458-1-HRP detected SRS 2 at a concentration of 100 pM. The other three conjugates were less effective, detecting SRS 2 to 1 nM. Thus, the 495-1-HRP conjugate would be used as the detection reagent in the immunoenzymometric assay for progastrin 6-80, using SRS 2, as run under the conditions of this example.

TABLE 6

Comparison of MAb 495-HRP conjugates as Detection Reagents in the Immunoenzymometric assay for Progastrin 6-80

| SRS 2 Peptide Concentration | Absorbance Values (background subtracted) | | | |
|---|---|---|---|---|
| | 495-1-HRP | 495-2-HRP | 495-3-HRP | 495-4-HRP |
| 100 μM | 3.407 | 0.788 | 3.220 | 0.809 |
| 10 μM | 2.324 | 0.855 | 1.437 | 0.671 |
| 1 μM | 2.721 | 0.977 | 1.117 | 0.582 |
| 100 nM | 1.856 | 0.814 | 0.857 | 0.571 |
| 10 nM | 1.431 | 0.359 | 0.470 | 0.254 |
| 1 nM | 0.462 | 0.012 | 0.096 | 0.029 |
| 100 pM | 0.053 | 0 | 0.007 | 0.003 |

Similar results were obtained when the four 495-HRP MAb conjugates were tested in the SRS 1 assay for progastrin 1-80, demonstrating the superiority of the 495-1-HRP conjugate in these assays.

Deposit of Hybridoma Cell Lines

The following hybridomas were deposited with the American Type Culture Collection (ATCC, Manassas, Va.) on Sep. 1, 2004:
1. Hybridoma 490-1 producing MAb 490-1 was assigned accession number PTA-6189.
2. Hybridoma 491-1 producing MAb 491-1 was assigned accession number PTA-6190.
3. Hybridoma 495-1 producing MAb 495-1 was assigned accession number PTA-6191.

Incorporation by Reference

The specifications of the U.S. patents and the texts of each of the references cited herein are hereby incorporated by reference in their entireties.

What is claimed is:

1. A pharmaceutical composition, comprising a progastrin-binding molecule that selectively binds to progastrin, wherein the molecule does not bind to gastrin-17 (G17), gastrin-34 (G34), glycine-extended gastrin-17 (G17-Gly) or glycine-extended gastrin-34 (G34-Gly), and wherein the progastrin-binding molecule selectively binds to the amino acid sequence SQQPDAPLG (SEQ ID NO:7).

2. The pharmaceutical composition of claim 1, wherein the progastrin-binding molecule comprises an antibody binding region.

3. The pharmaceutical composition of claim 1, wherein the progastrin-binding molecule is an antibody.

4. The pharmaceutical composition of claim 3, wherein the antibody is a monoclonal antibody.

5. The pharmaceutical composition of claim 3, wherein the antibody is a single chain antibody.

6. The pharmaceutical composition of claim 3, wherein the antibody is a mammalian antibody.

7. The pharmaceutical composition of claim 6, wherein the mammalian antibody is a murine antibody, a chimeric human/mouse antibody, a human antibody or a humanized antibody.

8. A monoclonal antibody, wherein the monoclonal antibody is selected from the group consisting of a monoclonal antibody that selectively binds to the amino acid sequence SQQPDAPLG (SEQ ID NO:7), a monoclonal antibody produced by hybridoma 495-1 (ATCC Accession No. PTA-6191), and a monoclonal antibody produced by hybridoma 490-1 (ATCC Accession No. PTA-6189).

9. The monoclonal antibody of claim 8, wherein the antibody binds the epitope bound by the monoclonal antibody produced by hybridoma 491-1 (ATCC Accession No. PTA-6190).

10. The monoclonal antibody of claim 8 that is a murine antibody, a chimeric human/mouse antibody, a human antibody or a humanized antibody.

11. A combination, comprising two or more monoclonal antibodies selected from the group consisting of a monoclonal antibody that binds to an epitope within the amino acid sequence SWKPRSQQP (SEQ ID NO:6), a monoclonal antibody that binds to an epitope within the amino acid sequence SQQPDAPLG (SEQ ID NO:7), and a monoclonal antibody produced by hybridoma 495-1 (ATCC Accession No. PTA-6191).

12. The combination of claim 11, further comprising one or more anti-gastrin monoclonal antibody.

13. The combination of claim 12, wherein the anti-gastrin monoclonal antibody selectively binds a gastrin hormone species selected from the group consisting of G17 and G34.

14. A hybridoma selected from the group consisting of hybridoma 490-1 (ATCC Accession No. PTA-6189), hybridoma 491-1 (ATCC Accession No. PTA-6190), and hybridoma 495-1 (ATCC Accession No. PTA-6191).

15. A pharmaceutical composition comprising a monoclonal antibody of claim 8 and a pharmaceutically acceptable carrier.

16. A progastrin immunoassay, comprising:
a) contacting a sample to be assayed for progastrin with a monoclonal antibody that specifically binds progastrin, but does not bind gastrin-17 (G17), gastrin-34 (G34), glycine-extended gastrin-17 (G17-Gly) or glycine-extended gastrin-34 (G34-Gly), under suitable conditions for antibody binding and allowing any progastrin present to form a progastrin-monoclonal antibody complex, wherein the monoclonal antibody is a monoclonal antibody of claim 8; and
b) detecting the presence or absence of the progastrin-monoclonal antibody complex by an immunodetection method.

17. The progastrin immunoassay of claim 16, wherein the monoclonal antibody binds the epitope bound by the monoclonal antibody produced by a hybridoma selected from the group consisting of hybridoma 490-1 (ATCC Accession No. PTA-6189), hybridoma 491-1 (ATCC Accession No. PTA-6190), and hybridoma 495-1 (ATCC Accession No. PTA-6191).

18. The progastrin immunoassay of claim 16, wherein the immunodetection method is any enzyme-linked immunosorption assay (ELISA), a radioimmunoassay (RIA), an immunohistochemistry (IHC) assay, an immunofluorescence (IF) assay, an agglutination assay, a western blot assay, a dot blot assay, a slot blot assay or a surface plasmon resistance detection method.

19. An immunoenzymometric assay, comprising:
(a) immobilizing a first monoclonal antibody on a support, wherein the first monoclonal antibody is selective for the N-terminus of human progastrin and is an antibody that selectively binds to an epitope within amino acid sequence SWKPRSQQP (SEQ ID NO:6) or an epitope within amino acid sequence SQQPDAPLG (SEQ ID NO:7);
(b) contacting a test sample to be assayed for progastrin with the immobilized monoclonal antibody to form complexes of any progastrin in the sample with the immobilized antibody;
(c) contacting the complexes with a second monoclonal antibody specific for the C-terminus of progastrin and produced by hybridoma 495-1 (ATCC Accession No. PTA-6191); and
(d) detecting the amount of the second monoclonal antibody bound on the support as indicative of the amount of progastrin present in the test sample.

20. The assay of claim 19, wherein the support is a test plate.

21. A method of diagnosing a gastrin-promoted disease or condition in a patient, comprising:
(a) performing an immunoassay of claim 16 to determine the level of progastrin in a sample of biological fluid from the patient; and
(b) comparing the level of progastrin in the sample with the level of progastrin in a sample of biological fluid from one or more control individuals, or with a reference standard, and, if different diagnosing the disease or condition.

22. A method of monitoring treatment of a gastrin-promoted disease or condition in a patient comprising:
(a) determining the level of progastrin in a first sample from a patient prior to or in the early stages of a treatment for a gastrin-promoted disease or condition by an immunoassay method of claim 16;
(b) determining the level of progastrin in a second sample from the patient after treatment is effected by an immunoassay method of claim 16; and
(c) comparing the amount of progastrin in the first sample with the amount of progastrin in the second sample to assess a change and thereby monitor treatment.

23. A monoclonal antibody produced by a hybridoma of claim 14.

24. A chimeric human/mouse antibody or humanized antibody produced from a monoclonal antibody produced by a hybridoma of claim 14.

25. A pharmaceutical composition comprising a monoclonal antibody produced by a hybridoma of claim 14 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,158,128 B2 | Page 1 of 1 |
| APPLICATION NO. | : 11/663126 | |
| DATED | : April 17, 2012 | |
| INVENTOR(S) | : Grimes | |

It is certified that error appears in the above-identified patent and that said Letters Patent is hereby corrected as shown below:

In the Specification

On column 6, line 23
  replace "plasmon resistance"
  with --plasmon resonance--.

On column 7, line 10
  replace "plasmon resistance"
  with --plasmon resonance--.

On column 11, line 13
  replace "plasmon resistance-type"
  with --plasmon resonance-type--.

On column 12, line 1
  replace "plasmon resistance"
  with --plasmon resonance--.

On column 14, line 22
  replace "plasmon resistance"
  with --plasmon resonance--.

In the Claims

On column 36, line 13
  replace "plasmon resistance"
  with --plasmon resonance--.

Signed and Sealed this
Twenty-second Day of July, 2014

Michelle K. Lee
*Deputy Director of the United States Patent and Trademark Office*